(12) United States Patent
Le

(10) Patent No.: US 7,803,554 B2
(45) Date of Patent: Sep. 28, 2010

(54) DETECTION OF BINDING FACTORS WITH FLUORESCENCE POLARIZATION

(76) Inventor: Xiao-Chun (Chris) Le, 11532 43rd Avenue, Edmonton, Alberta (CA) T6J 0Y5

(*) Notice: Subject to any disclaimer, the term of this patent is extended or adjusted under 35 U.S.C. 154(b) by 248 days.

(21) Appl. No.: 10/763,259

(22) Filed: Jan. 26, 2004

(65) Prior Publication Data
US 2005/0037377 A1 Feb. 17, 2005

Related U.S. Application Data

(63) Continuation of application No. 09/946,829, filed on Sep. 4, 2001, now abandoned.

(60) Provisional application No. 60/230,060, filed on Sep. 1, 2000.

(51) Int. Cl.
*G01N 33/53* (2006.01)
*C40B 40/10* (2006.01)

(52) U.S. Cl. ............... 435/7.1; 435/6; 435/4; 436/512; 436/161

(58) Field of Classification Search ............ 435/7.1, 435/6, 4, DIG. 3; 436/512, 161
See application file for complete search history.

(56) References Cited

U.S. PATENT DOCUMENTS 6,132,968 A * 10/2000 Le et al. ............... 435/6
6,303,337 B1 * 10/2001 Rothschild et al. ......... 435/69.1
6,331,392 B1 * 12/2001 Laing et al. ............... 435/6

OTHER PUBLICATIONS

Wan et al. Anal. Chem. 2000, 72, 5583-89.*
Bandyopadhyay, P.K., et al., *Biochemistry*, (1978), vol. 17, No. 19, 4078-4085.
Booth, E.D., et al., *Carcinogenesis*, vol. 15, No. 10, (1994), 2099-2106.
Brinkley, M., *Bioconjugate Chem.*, vol. 3, No. 1, (1992), 2-13.
Carey, J., *Proc. Natl. Acad. Sci.*, USA, vol. 85, (1988), 975-979.
Chase, J.W., et al., *Annu. Rev. Biochem.* vol. 55, (1986), 103-136.
Chen, F.T., et al., *Electrophoresis*, vol. 15, (1994), 13-21.
Chiem, N.H., et al., *Clin. Chem.*, vol. 44, (1998), 591-598.
Chu, Y.-H., et al., *Acc. Chem. Res.*, vol. 28, (1995), 461-468.
Cosman, M., et al., *Carcinogenesis*, vol. 11, No. 9, (1990), 1667-1672.
Craig, D.B., et al., *Anal. Chem.*, vol. 70, (1998), 2493-2494.
Crawford, I.P., et al., *Ann. Rev. Biochem.*, vol. 49, (1980), 163-195.
Dandliker, W.B., et al., *Immunochemistry*, Vo. 7, (1970), 799-828.

Evangelista, R.A., et al., *J. Chromatogr.* A, vol. 680, (1994), 587-591.
Fey, H., et al., *J. Clin. Microbiol.*, Vo. 19, (1984), 34-38.
Funk, M., et al., (1997) *Bioconjugate Chem.* 8, 310-317.
German, I., et al., *Anal. Chem.*, vol. 70, (1998), 4540-4545.
Gottfried, D.S., et al., *J. Phys. Chem. B.*, vol. 103, (1999), 2803-2807.
Guo, X.-Q., et al., *Anal. Chem.*, vol. 70, (1998), 632-637.
Hamdan, I.I., et al., *Nucleic Acids Res.*, vol. 26, (1998), 3053-3058.
Haugland, R.P., *Handbook of Fluorescent Probes and Research Chemicals*; 6th Edition; Molecular Probes: Eugene, (1996), p. 20.
Hsu, T.M., et al., *Carcinogenesis*, vol. 16, (1995), 2263-2265.
Johnson, H.M., et al., *Appl. Microbiol.*, vol. 26, (1973), 309-313.
Karger, B. L., et al., *J. Chromatogr.*, vol. 492, (1989), 585-614.
Krauss, G., et al., *Biochemistry*, vol. 20, (1981), 5346-5352.
Lam, M.T., et al., *J. Chromatogr A.*, vol. 853, (1999), 545-553.
Lawson, C.L., et al., *Nature*, vol. 366, (1988), 178-182.
Le, X.C., et al., *Science*, vol. 280, (1998), 1066-1069.
LeTilly V., et al., *Biochemistry*, vol. 32, (1993), 7753-7758.
Lee, M. H., et al., *J. Clin. Microbiol.*, vol. 25, (1987), 1717-1721.
Lohman, T.M., et al., *Annu. Rev. Biochem.*, vol. 63, (1994), 527-570.
Margulis, L.A., et al., *Chem. Res. Toxicol.*, vol. 6, (1993), 59-63.
Marrack, P., et al., *Science*, vol. 248, (1990), 705-711.
Molineux I.J., et al., *Nucleic Acids Res.*, vol. 2, (1975), 1821-1837.
Otwinowski, Z., et al., *Nature*, vol. 335, (1988), 321-329.
Perrin, F. J., *Phys. Radium*, vol. 7, (1926), 390-401.
Santella, R.M., et al., *Carcinogenesis*, vol. 15, (1984), 373-377.
Scatchard, G., *Ann. NY Acad. Sci. USA*, vol. 51, (1949), 660-672.
Schantz, E.J., et al., *Biochemistry*, vol. 11, (1972), 360-366.
Schmalzing, D., et al., *Anal. Chem.*, vol. 67, (1995), 606-612.
Schutz, N.M., et al., *Anal.Chem.* (1995) 67, 924-929.
Schwenzer, K.S., et al., *Ther. Drug Monit.* (1983), 5, 341-345.
Shimura, K., et al., *Anal. Chem.* vol. 66, (1994), 9-15.
Stebbins, M.A., et al., *J. Chromatogr. B*, vol. 683, (1996), 77-84.
Tan, W.G., et al., *J. Chromatogr. A*, vol. 924, (2001), 377-386.
Tao, L., et al., *Anal. Chem.*, vol. 68, (1996), 3899-3906.
Thompson, N. E., et al., *Appl. Environ. Microbiol.*, vol. 51, (1986), 885-890.
Wan, Q.-H., et al., *Anal. Chem.*, vol. 71, (1999), 4183-4189.
Wan, Q.-H, et al., *J. Chromatogr. A*, vol. 853, (1999), 555-562.
Weber, G., *Adv. Protein Chem.*, vol. 8, (1953), 415-459.
Xing, J.Z., et al., *Methods in Molecular Biology*, vol. 162, (2001), 419-428.
Ye, L., et al., J. Chromatogr. B, vol. 714, (1998), 59-67.
Zhang, H., et al., *Mol. Biol.*, vol. 238, (1994), 592-614.

* cited by examiner

*Primary Examiner*—Teresa D. Wessendorf
(74) *Attorney, Agent, or Firm*—Buchanan Ingersoll & Rooney PC

(57) ABSTRACT

This invention relates to a simple and quick method for the detection, identification and/or quantitation of binding factors using fluorescence techniques. A fluorescent probe is incubated with a factor or group of factors, and the presence of a factor capable of binding the probe can be detected by fluorescence polarization. When coupled with a separation step, this invention allows on-line monitoring of binding complex formation.

5 Claims, 1 Drawing Sheet

SEQUENCE LISTING

<160> NUMBER OF SEQ ID NOS: 11

<210> SEQ ID NO 1
<211> LENGTH: 11
<212> TYPE: DNA
<213> ORGANISM: Artificial Sequence
<220> FEATURE:
<223> OTHER INFORMATION: Fluorescein oligonucleotides

<400> SEQUENCE: 1
cgcgatacgc c                                                          11

<210> SEQ ID NO 2
<211> LENGTH: 37
<212> TYPE: DNA
<213> ORGANISM: Artificial Sequence
<220> FEATURE:
<223> OTHER INFORMATION: Fluorescein oligonucleotides

<400> SEQUENCE: 2
ccttaagctt cctcaaccac ttaccatact cgagatt                              37

<210> SEQ ID NO 3
<211> LENGTH: 84
<212> TYPE: DNA
<213> ORGANISM: Artificial Sequence
<220> FEATURE:
<223> OTHER INFORMATION: Fluorescein oligonucleotides

<400> SEQUENCE: 3
atctactgga ttagcgatac tcgattaggt cccctgccgc taaaccatac cgcggtaact     60
tgagcaaaat caccactgca gggg                                            84

<210> SEQ ID NO 4
<211> LENGTH: 81
<212> TYPE: DNA
<213> ORGANISM: Artificial Sequence
<220> FEATURE:
<223> OTHER INFORMATION: Fluorescein oligonucleotides

<400> SEQUENCE: 4
atccgcctga ttagcgatac ttacgtgagc gtgctgtccc ctaaaggtga tacgtcactt     60
gagcaaaatc acctgcaggg g                                               81

<210> SEQ ID NO 5
<211> LENGTH: 16
<212> TYPE: DNA
<213> ORGANISM: Artificial Sequence
<220> FEATURE:
<223> OTHER INFORMATION: Fluorescein oligonucleotides

<400> SEQUENCE: 5
cccattatgc ataacc                                                     16

<210> SEQ ID NO 6
<211> LENGTH: 31
<212> TYPE: DNA
<213> ORGANISM: Artificial Sequence
<220> FEATURE:
<223> OTHER INFORMATION: Fluorescein oligonucleotides

<400> SEQUENCE: 6
gagtatggta agtggttgag gaagcttaag g                                    31

<210> SEQ ID NO 7
<211> LENGTH: 30
<212> TYPE: DNA
<213> ORGANISM: Artificial Sequence
<220> FEATURE:
<223> OTHER INFORMATION: Fluorescein oligonucleotides

<400> SEQUENCE: 7
catatgacgg ttatgcataa tgggaatctc                                      30

<210> SEQ ID NO 8
<211> LENGTH: 37
<212> TYPE: DNA
<213> ORGANISM: Artificial Sequence
<220> FEATURE:
<223> OTHER INFORMATION: Fluorescein oligonucleotides

<400> SEQUENCE: 8
gtcatatgcc gcctctgacc ttcctagaat tccatcc                              37

<210> SEQ ID NO 9
<211> LENGTH: 29
<212> TYPE: DNA

-continued

```
<213> ORGANISM: Artificial Sequence
<220> FEATURE:
<223> OTHER INFORMATION: Fluorescein oligonucleotides

<400> SEQUENCE: 9
ggatggaatt ctaggaaggt cagaggcgg                                29

<210> SEQ ID NO 10
<211> LENGTH: 25
<212> TYPE: DNA
<213> ORGANISM: Artificial Sequence
<220> FEATURE:
<223> OTHER INFORMATION: Fluorescein oligonucleotides

<400> SEQUENCE: 10
atcgaactag ttaactagta cgcaa                                    25

<210> SEQ ID NO 11
<211> LENGTH: 25
<212> TYPE: DNA
<213> ORGANISM: Artificial Sequence
<220> FEATURE:
<223> OTHER INFORMATION: Fluorescein oligonucleotides

<400> SEQUENCE: 11
tagcttgatc aattgatcat gcgtt                                    25
```

DETECTION OF BINDING FACTORS WITH FLUORESCENCE POLARIZATION

CROSS-REFERENCE TO RELATED APPLICATIONS

This application is a continuation of U.S. application Ser. No. 09/946,829, filed on Sep. 4, 2001, now abandoned which claims priority under 35 U.S.C. §119 to U.S. Provisional Application No. 60/230,060, filed on Sep. 1, 2000, the entire contents of which are hereby incorporated by reference.

RELATED APPLICATIONS

This application claims the benefit of U.S. application Ser. No. 60/230,060, filed Sep. 1, 2000, which is hereby incorporated by reference in its entirety.

FIELD OF THE INVENTION

This invention relates to methods of detection, identification and quantitation of binding factors with fluorescence techniques.

REFERENCES

U.S. Pat. No. 6,132,968.
Baker, D. R., *Capillary Electrophoresis*, John Wiley & Sons: New York; 1995; Chapter 2.
Bandyopadhyay; P. K., et al., *Biochemistry* (1978), 17, 4078-4085.
Barrett, C. H., in *Antibody Techniques*; Malik, V. S.; Lillehoj, E. P., Eds.; Academic Press: San Diego, 1994; pp 71-102.
Booth, E. D., et al., (1994) *Carcinogenesis* 15, 2099-2106.
Brinkley, M., *Bioconjugate Chem.* (1992), 3, 2-13.
Carey, J. *Proc. Natl. Acad. Sci. USA* (1988), 85, 975-979.
Chase, J. W., et al., *Annu. Rev. Biochem.* (1986), 55, 103-136.
Chen, F. T. et al., *Electrophoresis* 15 (1994) 13-21.
Chiem, N. H., et al., *Clin. Chem.* 44 (1998) 591-598.
Chu, Y.-H., et al., *Acc. Chem. Res.* (1995), 28, 461-468.
Cosman, M., et al., (1990) *Carcinogenesis* 11, 1667-1672.
Craig, D. B., et al., *Anal. Chem.* (1998), 70, 2493-2494.
Crawford, I. P., et al., *Ann. Rev. Biochem.* (1980), 49, 163-95.
Dandliker, W. B., et al., *Immunochemistry* (1970) 7, 799-828.
Evangelista, R. A., et al., *J. Chromatogr. A* 680 (1994) 587-591.
Fey, H., et al., *J. Clin. Microbiol.* (1984), 19, 34-38.
Funk, M., et al., (1997) *Bioconjugate Chem* 8, 310-317.
German, I., et al., *Anal. Chem.* (1998), 70, 4540-4545.
Gottfried, D. S., et al., *J. Phys. Chem. B* (1999), 103, 2803-2807.
Guo, X.-Q., et al., *Anal. Chem.* (1998), 70, 632-637.
Hamdan, I. I., et al., *Nucleic Acids Res.* (1998), 26, 3053-3058.
Haugland, R. P. *Handbook of Fluorescent Probes and Research Chemicals; 6th Edition*; Molecular Probes: Eugene, 1996; p 20.
Hsu, T. M., et al., (1995) *Carcinogenesis* 16, 2263-2265.
Johnson, H. M., et al., *Appl. Microbiol.* (1973), 26, 309-313.
Karger, B. L. et al., *J. Chromatogr.* 492 (1989) 585-614.
Krauss, G., et al., *Biochemstry* (1981), 20, 5346-5352.
Lakowicz, J. R., *Principles of Fluorescence Spectroscopy*; Plenum Press: New York, 1983.
Lakowicz, J. R. *Principles of Fluorescence Spectroscopy*; Kluwer Academic/Plenum: New York, 2$^{nd}$ Ed., 1999.
Lam, M. T., et al., (1999) *J Chromatogr A* 853, 545-553.
Lawson, C. L., et al., *Nature* (1988), 366, 178-182.
Le, X. C., et al., (1998) *Science* 280, 1066-1069.
LeTilly, V., et al., *Biochemistry* (1993), 32, 7753-7758.
Lee, M. H., et al., *J. Clin. Microbiol.* (1987), 25, 1717-1721.
Lohman, T. M., et al., *Annu. Rev. Biochem.* (1994), 63, 527-570.
Margulis, L. A., et al., (1993) *Chem Res Toxicol* 6, 59-63.
Marrack, P., et al., *Science* (1990), 248, 705-711.
Molineux, I. J., et al., *Nucleic Acids Res.* (1975), 2, 1821-1837.
Motulsky, H., *Analyzing Data with GraphPad Prism*, GraphPad Software: San Diego, Calif., 1999; p 173.
Nix, B.; Wild, D., in "*Immunoassay*" (edited by Gosling, P. J.), Oxford University Press, 2000. p 246.
Otwinowski, Z., et al., *Nature* (1988), 335, 321-329.
Perrin, F. J., *Phys. Radium* (1926), 7, 390-401.
Pfeifer, G. P., (Editor), *Technologies for Detection of DNA Damage and Mutations*, Plenum Press, New York, 1996.
Santella, R. M., et al., *Carcinogenesis* 15 (1984) 373-377.
Scatchard, G., *Ann. NY Acad. Sci. USA*, (1949, 51, 660.
Schantz, E. J., et al., *Biochemistry* (1972), 11, 360-366.
Schmalzing, D., et al., *Anal. Chem.* 67 (1995) 606-612.
Schultz, N. M., et al., *Anal. Chem.* (1993), 65, 3161-3165.
Schulz, N. M., et al., *Anal. Chem.* 67 (1995) 924-929.
Schwenzer, K. S., et al., *Ther. Drug Monit.* (1983), 5, 341-345.
Shimura, K., et al., *Anal. Chem.* (1994), 66, 9-15.
Stebbins, M. A, et al., *J. Chromatogr. B* (1996), 683, 77-84.
Stebbins, M. A., et al., *J. Chromatogr., B* (1996), 683, 3053-3058.
Tan, W. G., et al., (2001) *J. Chromatogr. A* 924, 377-386.
Tao, L., et al., (1996) *Anal. Chem.* 68, 3899-3906.
Thompson, N. E., et al., *Appl. Environ. Microbiol.* (1986), 51, 885-890.
Wan, Q.-H., et al., *Anal. Chem.* (1999), 71, 4183.
Wan, Q. H., et al., (1999) *J. Chromatogr. A* 853, 555-562.
Wang, H., et al., (2001) *Submitted to Anal. Chem.*
Weber, G. *Adv. Protein Chem.* (1953), 8, 415-459.
Xing, J. Z., et al., (2001) *Methods in Molecular Biology* 162, 419-428.
Ye, L., et al., *J. Chromatogr. B* (1998), 714, 59-67.
Ye, L., et al., (1998) *J. Chromatogr. B* 714, 59-67.
Zhang, H, et al., *Mol. Biol.* (1994), 238, 592-614.

All of the above publications, patents and patent applications are herein incorporated by reference in their entirety to the same extent as if the disclosure of each individual publication, patent application or patent was specifically and individually indicated to be incorporated by reference in its entirety.

BACKGROUND OF THE INVENTION

Affinity binding complex formation is an essential step in biological or pharmaceutical phenomena. For example, the binding of proteins to DNA underlines many cellular activities including the control of gene expression, site-specific recombination, replication and repair of DNA damage. Enzyme-substrate interactions involve the recognition and binding of substrate by the enzyme as the first step. Hormones, neurotransmitters, lymphokines and other effector molecules bind to their receptors to initiate the cellular process which ultimately lead to achievement of their functions.

Consequently, affinity binding complexes are also important tools in biological or pharmaceutical research. For example, drug discovery often involves identification of binding factors of a particular target which mediates a disease. A variety of methods have been employed to detect affinity binding complex formation in order to identify the binding factors. For example, the gel electrophoresis mobility shift assay (EMSA) is the most commonly used method in the study of protein-DNA interactions. This method is based on the observation that binding of a protein to DNA fragments leads to a reduction in the electrophoretic mobility of the DNA fragment in non-denaturing polyacrylamide or agarose gels. While used extensively, EMSA requires relatively large amounts of sample and lengthy analysis time. Moreover, the assay is not suitable when dissociation of protein-DNA complex occurs during gel electrophoresis.

As another example, capillary electrophoresis (CE) combined with affinity recognition has gained a tremendous growth in recent years, with increasing biochemical, clinical, and pharmaceutical applications. A key element of the technique is the use of a molecular recognition agent, typically a protein that binds to a target molecule with high specificity and affinity. The complex formation can occur either before or during the electrophoretic separation, depending on the stability of the resultant complex. In applications such as CE-based immunoassays, however, tight binding of the analyte to the protein is essential to achieve a high degree of sensitivity and reproducibility. Ideally, the affinity complex thus formed should remain intact throughout the electrophoretic separation.

In current practice of affinity CE, the formation and stability of the complex are usually established by titration experiments, in which a series of solutions containing the substrate and its binding protein in various ratios are analyzed. The emergence of a new peak upon addition of the binding protein to the substrate is taken as the evidence for complex formation and the relative intensities corresponding to the complex and the free substrate are used for quantitation. The titration experiments have proved to be very useful in studies of binding interactions; however, they are time-consuming and unable to provide unequivocal identification of the complex when the complex is not well separated from the unbound molecules. Therefore, there remains a need for a simple and sensitive method to detect affinity complex formation.

SUMMARY OF THE INVENTION

This invention is directed to a simple method based on laser-induced fluorescence polarization (LIFP) detection of an affinity complex of a fluorescent probe and its binding factor. The affinity complexes are readily distinguished from the unbound molecules on the basis of their fluorescence polarization, which is sensitive to changes in the rotational diffusion characteristics arising from molecular association or dissociation. The relative increase in fluorescence polarization upon complex formation varied with the molecular size of the binding pairs. A small molecule rotates fast in solution and exhibits a low value of polarization whereas a large molecule exhibits a higher polarization because of its slower motion under the same conditions. Thus, changes in fluorescence polarization can reflect the association or dissociation status between molecules of interest. When combined with capillary electrophoresis or other suitable separation procedures, this method allows for on-line monitoring of affinity complex formation.

Accordingly, an aspect of this invention is directed to a method for detecting a binding factor for a probe, comprising:
  (a) labeling the probe with a fluorophore;
  (b) incubating the labeled probe with a factor or a group of factors which may bind the labeled probe to form a binding complex;
  (c) separating the binding complex and the free probe into different fractions; and
  (d) subjecting each fraction from step (c) to fluorescence polarization measurement under conditions wherein the binding complex produces a fluorescence pattern different from that of the free probe, thereby allowing detection of the binding complex.

The separation step may be performed simultaneously with, or prior to, the fluorescence polarization detection step. The free probe and the bound probe may be separated by any method which is compatible with fluorescence polarization. Preferably, the separation method is capable of being performed in liquid phase. The separation method is more preferably liquid chromatography or electrokinetic chromatography, and most preferable capillary electrophoresis or capillary gel electrophoresis.

In another aspect of the present invention, this method can be applied to screen a chemical compound library, such as combinatorial library. Thus, in order to identify a compound which is capable of binding to a molecule of interest, the molecule of interest is used as a probe and labeled with a fluorophore. The labeled probe is then incubated with a compound library and the whole mixture can be analyzed by fluorescence polarization. Alternatively, the mixture is separated with a suitable method. The fractions are monitored on-line with fluorescence polarization which can distinguish the free probe from the bound probe, thereby identify whether there is a binding compound in the particular fraction.

Similarly, this method can also be applied to screen a mixture of natural products, such as a cell lysate or a homogenate of tissue. The natural products may come from any source, including animals, plants and microorganisms.

In another aspect of this invention, the method can be used to determine if a particular sequence or modification exists in a DNA. For example, exposure to certain carcinogens induce alkylation or other kinds of modification of DNA, which may result in mutations and abnormal gene expression to cause cancer formation. By using a specific probe which binds to a certain DNA sequence or modification, one can detect if this sequence or modification exists in the genomic DNA for diagnosis purposes.

The probe can be a protein (including peptides), particularly antibodies, enzymes and cell surface receptors. The probe can also be a nucleic acid, carbohydrate or carbohydrate derivatives, small organic or inorganic compounds, or any molecule which can be labeled with a fluorophore or is naturally fluorescent. The probe is preferably less than about 15,000 daltons in molecular weight, more preferably less than about 10,000 daltons, yet more preferably less than about 5,000 daltons, still more preferably less than about 3,000 daltons, and most preferably less than about 1,500 daltons.

In yet another aspect, this invention provides a method to determine the binding affinity or stoichiometry of an affinity complex.

In addition, this invention can also be used to monitor the formation of fluorescently labeled molecules, which may be used as probes in the present method but are not limited to such use. Labeling of molecules with a fluorophore is often required for high sensitivity quantitation and detection of the molecules. However, it is difficult to identify whether the desired molecule is labeled or what the labeling efficiency is. This invention provides a fast method to monitor the labeling process since the labeled molecule can be readily differentiated from the free fluorephore because of their difference in fluorescence polarization.

Figure 1:
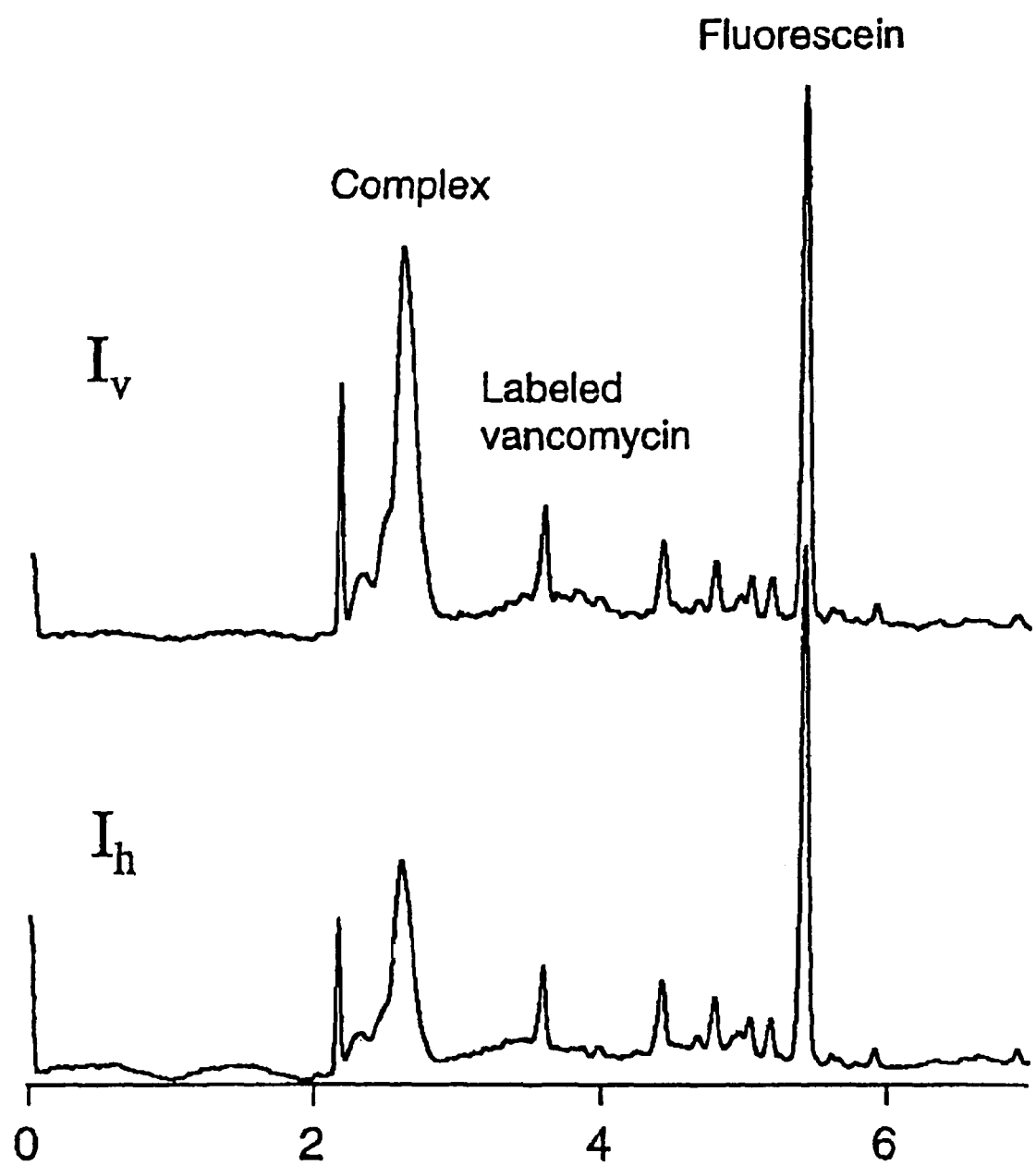
FIG. 1

Electropherograms showing vertically and horizontally polarized fluorescence of the complex formed between fluorescein-labeled vancomycin and its antibody. A 35 cm long, 20 mm i.d., fused silica capillary was used for separation with a 25 mM disodium tetraborate (pH 9.1) as the running buffer. The separation voltage was 25 kV. Fluorescence detection was post-capillary with vertically polarized excitation at 488 nm. Iv and Ih correspond to vertically and horizontally polarized fluorescence intensity, respectively, measured at 515 nm.

DETAILED DESCRIPTION OF THE INVENTION

This invention relates to a simple and quick method for the detection, identification and/or quantitation of binding factors using fluorescence techniques. A fluorescent probe is incubated with a factor or group of factors, and the presence of a factor capable of binding the probe can be detected by fluorescence polarization. When coupled with a separation step, this invention allows on-line monitoring of binding complex formation.

Prior to describing the invention in further detail, the terms used in this application are defined as follows unless otherwise indicated.

Definitions

As used herein, a "probe" can be any molecule or substance for which it is desired to find a binding factor. Examples of a probe include proteins, peptides, nucleic acids, carbohydrates or carbohydrates derivative, and small organic or inorganic compounds.

As used herein, a "fluorophore" is any fluorescent substance, for example, fluorescein.

As used herein, "a factor or a group of factors" means a substance or a mixture of substance of any nature. A factor may be a protein, a peptide, a nucleic acid, a carbohydrate or carbohydrate derivative or any other organic or inorganic compound. A group of factors may be a mixture of factors of the same nature., or a mixture of factors of different natures. For example, a cell lysate or homogenate is a group of factors which contains proteins, carbohydrates, lipids, nucleic acids, and any other substance contained in a cell or cells.

As used herein, a nucleic acid "modification" refers to any change in the structure of the nucleic acid sequence. Changes in the structure of a nucleic acid sequence include changes in the covalent and non-covalent bonds in the nucleic acid sequence. Illustrative of these changes are mutations, mismatches, strand breaks, as well as covalent and non-covalent interactions between a nucleic acid sequence, which contains unmodified and/or modified nucleic acids, and other molecules. Illustrative of a covalent interaction between a nucleic acid sequence and another molecule are changes to a nucleotide base (e.g., formation of thymine glycol) and covalent cross-links between double-stranded DNA sequences which are introduced by ultraviolet radiation or by cis-platinum. Yet another example of a covalent interaction between a nucleic acid sequence and another molecule includes covalent binding of two nucleic acid sequences to psoralen following ultraviolet irradiation. Non-covalent interactions between a nucleic acid sequence and another molecule include non-covalent interactions of a nucleic acid sequence with a molecule other than a nucleic acid sequence and other than a polypeptide sequence. Non-covalent interactions between a nucleic acid sequence with a molecule other than a nucleic acid sequence and other than a polypeptide sequence are illustrated by non-covalent intercalation of ethidium bromide or of psoralen between the two strands of a double-stranded deoxyribnucleic acid sequence.

As used herein, the term "mutation" refers to a deletion, insertion, or substitution. A "deletion" is defined as a change in a nucleic acid sequence in which one or more nucleotides is absent. An "insertion" or "addition" is that change in a nucleic acid sequence which has resulted in the addition of one or more nucleotides. A "substitution" results from the replacement of one or more nucleotides by a molecule which is different molecule from the replaced one or more nucleotides. For example, a nucleic acid may be replaced by a different nucleic acid as exemplified by replacement of a thymine by a cytosine, adenine, guanine, or uridine. Alternatively, a nucleic acid may be replaced by a modified nucleic acid as exemplified by replacement of a thymine by thymine glycol.

The term "mismatch" refers to a non-covalent interaction between two nucleic acids, each nucleic acid residing on a different nucleic acid sequence, which does not follow the base-pairing rules. For example, for the partially complementary sequences 5'-AGT-3' and 5'-AAT-3', a G-A mismatch is present.

The term "strand break" when made in reference to a double stranded nucleic acid sequence includes a single-strand break and/or a double-strand break. A single-strand break refers to an interruption in one of the two strands of the double stranded nucleic acid sequence. This is in contrast to a double-strand break which refers to an interruption in both strands of the double stranded nucleic acid sequence. Strand breaks may be introduced into a double stranded nucleic acid sequence either directly (e.g., by ionizing radiation) or indirectly (e.g., by enzymatic incision at a nucleic acid base).

As used herein, a "sample" may be a biological sample or an environmental sample. Environmental samples include material from the environment such as soil and water. Biological samples may be animal (e.g., human), fluid (e.g., blood, plasma and serum), solid (e.g., stool), tissue, liquid foods (e.g., milk), and solid foods (e.g., vegetables). A biological sample may comprise a cell, tissue extract, body fluid, chromosomes or extrachromosomal elements isolated from a cell, genomic DNA, RNA, cDNA and the like.

Methods

In the present invention, fluorescence polarization is used to distinguish between a fluorescently-labeled probe and a complex containing both the probe and a factor which binds the probe. The complex exhibits higher polarization than the probe because a small molecule, such as the probe, rotates freely in solution and tends to yield no polarization. However, when the probe is bound by another factor and the size of the complex is significantly larger than the free probe, the complex rotates much less freely, resulting in significantly higher polarization.

Accordingly, the molecular weight of the probe useful in the present invention should be less than about 20,000 daltons. A larger molecule will generate sizable polarization, making any increase in polarization more difficult to detect. Furthermore, since the size increase upon forming a complex to such a large probe is relatively less significant, it is also harder to further increase the polarization. Preferably, the probe has a molecular weight of less than 15,000 daltons. The molecular weight is more preferably less than about 10,000 daltons, yet more preferably less than about 5,000 daltons, still more preferably less than about 3,000 daltons, and most preferably less than about 1,500 daltons.

The probe can be a protein, nucleic acid, carbohydrate, lipid, or any molecule which can be labeled with a fluorophore. In particular, peptides, oligonucleotides and oligosaccharides are good probes due to their small sizes and easy synthesis. If an antibody is a candidate for a probe, it is preferable to use a fragment of the antibody, such as an Fab fragment, rather than the entire antibody.

The present method can be practiced with or without separation of the binding complex and the probe. Thus, the entire incubation mixture can be subjected to fluorescence polarization without separation, and the polarization pattern is compared to that of the probe alone. An increase in polarization would indicate the presence of at least one binding factor in the sample used to bind the probe.

Alternatively, the incubation mixture can be separated according to any method known in the art, and then subjected to polarization. In this case, the free probe and the complex will appear in two different fractions, and the identification of each fraction can be determined according to the polarization measurement (i.e, the complex has significantly higher polarization than the free probe). It is also possible to run the free probe alone by the same separation method as an indicator to determine which fraction contains the free probe. Once the position of the free probe is known, the complex can simply be detected and quantitated by fluorescence measurement, such as laser-induced fluorescence (LIF), without polarization.

It is preferable to separate the free probe from the complex in the present invention. One reason is that the sensitivity with which to detect the complex is much higher if the method contains a separation step. When the entire incubation mixture is subjected to polarization, the signal from the free probe is mixed with that from the complex, and the net increase in polarization may not be very conspicuous. This is particularly a problem if the probe is relatively large, resulting in a substantial background polarization. If the free probe is separated from the complex, the background noise arising from the free probe is eliminated, and polarization due to complex formation can be detected with higher sensitivity.

A common problem with separating binding complexes is that weak binding complexes tend to dissociate during separation. For example, in the mobility shift method of detecting binding complexes, an incubation mixture is separated by gel electrophoresis, and the position of the complex is then located by detecting the label contained in the probe. However, due to the pH, temperature or electronic field to which a complex is exposed during electrophoresis, a weak complex may dissociate during electrophoresis. If so, the location of the probe would be mistakenly interpreted as the location of the complex.

This problem is not a concern in the present invention. Since the fluorescence polarization measurement is very different between a complex and a free probe, it can be determined with significant certainty whether a fraction contains a complex or a free probe. Furthermore, the present invention can be used to monitor complex formation on-line during the course of the separation. Therefore, the presence of a complex can be detected before it dissociates.

A particular interesting application of the present invention is library screening. It is common to screen a large number of chemical compound libraries for a binding factor. Since the present invention enables one to quickly determine if a binding factor exists in a library or not, without having to separate the free probe and the complex, it is very useful in the initial screening. Once it has been determined which libraries contain binding factors, the incubation mixtures containing the libraries of interest can be separated using an appropriate method, and the present invention can again be used to locate the fractions having the complex, thereby allowing identification of the binding factors.

Another particular application of the present invention is to detect nucleic acid damages. Nucleic acid damages, such as mismatches, breaks or the formation of DNA adducts, often occur after the nucleic acid is exposed to carcinogens. The present invention can be used to detect nucleic acid damages using a factor which is capable of binding damaged nucleic acids. Thus, a sample suspected of having damaged nucleic acids can be incubated with a binding factor as well as a fluorescently labeled oligonucleotide probe harboring the specific nucleic acid damage. The binding complex between the probe and the binding factor can be detected using the present invention, with or without separation. If the sample contains the damage of interest, it would compete with the probe for the binding factor to result in a decrease in binding complex formation between the probe and the factor.

Any factor capable of binding specifically to a damaged nucleic acid can be used in the present invention, such as any antibody which recognizes a specific DNA adduct; the UvrA and UvrB proteins which bind UV dimers, polycyclic aromatic hydrocarbon adducts, cis-platinum adducts, aflatoxin adducts, psoralen adducts, anthramycin adducts, mitomycin C adducts, N-acetoxy-2-amino fluorene adducts, and N-hydroxy-2-aminofluorene adducts; the DNA-dependent protein kinase which specifically bind to DNA double strand ends; poly(ADP-ribose) polymerase which binds to single-strand breaks and double-strand breaks; and the MutS protein which binds to several different mismatches (see, e.g. U.S. Pat. No. 6,132,968).

The following examples are offered to illustrate this invention and are not to be construed in any way as limiting the scope of the present invention.

EXAMPLES

In the examples below, the following abbreviations have the following meanings. Abbreviations not defined have their generally accepted meanings.

° C.=degree Celsius
hr=hour
min=minute
µM=micromolar
mM=millimolar
M=molar
ml=milliliter
µl=microliter
mg=milligram
µg=microgram
PAGE=polyacrylamide gel electrophoresis
rpm=revolutions per minute
FBS=fetal bovine serum
DTT=dithiothrietol
PBS=phosphate buffered saline
CE=capillary electrophoresis
LIFP=laser induced fluorescence polarization
LIF=laser induced fluorescence
PMT=photomultiplier tube
SSB=single-stranded DNA binding protein
FITC=Fluorescein isothiocyanate
SEA=staphylococcal enterotoxin A
FPIA=fluorescence polarization immunoassay
IAF=5-iodoacetamidofluorescein
RT=reverse transcriptase
TBE=Tris-borate-EDTA
FAM=carboxyfluorescein
AMV=avian myeloblastosis virus
MMLV=Moloney murine leukemia virus
BPDE=benzo[a]pyrene diol epoxide
TMR=tetramethylrhodamine
EOF=electroosmatic flow
LED=light-emitting diode
DMEM=Dulbecco's modified Eagle's medium
DMSO=dimethylsulfoxide

Section A:

Examples 1-6

Application of the Present Invention in Complex Formation Between Various Biological Molecules Instrumentation. A laboratory-built capillary electrophoresis with laser induced fluorescence polarization (CE/LIFP) detection system was used (Ye, et al., 1998). Electrophoresis was performed using a high voltage power supply (Model CZE 1000R, Spellman, Plainview, N.Y.) and a fused silica capillary (Polymicro Technologies, Phoenix, Ariz.). The detection end of the capillary was inserted in a sheath flow cuvette (NSG Precision Cells, Farmingdale, N.Y.). A plane polarized laser beam from an argon ion laser (Model 2014-65 mL, Uniphase, San Jose, Calif.) was filtered through a laser line filter (488 nm, 10-nm band width, Newport, Fountain Valley, Calif.) and was used for excitation. The light emitted during fluorescence was collected with a 60× microscope objective lens (0.7 NA, Universe Kogaku, Oyster Bay, N.Y.), filtered with a narrow bandpass filter (515 nm, 10-nm band width, Newport), and passed through a pinhole. The emitted light was subsequently split with a broadband polarizing beamsplitter cube (Melles Griot, Irvine, Calif.) into vertically and horizontally polarized components, which were detected with two photomultiplier tubes (PMT1 and PMT2, R1477, Hamamatsu, Japan). The operation of the power supply and the acquisition of data were controlled by a Power Macintosh computer with an application software written in LabView (National Instruments, Austin, Tex.).

There is no fundamental difference between this apparatus and the conventional fluorescence detectors that are also capable of anisotropy measurements. The only difference is that our cuvette (flow cell) is much smaller (0.2×0.2 square) than commercially available cells and that our detector is capable of handling the small volumes suitable for CE separation.

CE/LIFP Analysis. Unless otherwise stated the CE/LIFP were run as follows. A capillary of 20 mm i.d, 148 mm o.d. and 35 cm in length was used in conjunction with 25 mM $Na_2B_4O_7$ (pH 9.1) as a typical running buffer. Prior to sample analysis, the capillary was preconditioned periodically by successive rinsing with 0.1 M NaOH, deionized water and the running buffer to ensure reproducibility of the separation. Samples were electrokinetically injected into the capillary by applying an electric field of 143 V/cm for 5 s. Separation was carried out under an electric field of 714 V/cm. The electrophoretic mobility (m) of a solute was calculated using the following equation (Haugland, 1996; Schantz, et al., 1972).

$$m = L(1/t_{eo} - 1/t)/E \tag{1}$$

where L and E are the capillary length and applied electric field strength; $t_{eo}$ and t are the migration times of the solvent and solute, respectively.

Horizontally and vertically polarized fluorescence intensities measured by the LIFP detector were optimized by aligning a tightly focused laser beam with a small-diameter sample stream and by balancing signals from the two PMTs. An aqueous solution of disodium fluorescein ($10^{-9}$ M) was passed through a capillary inserted in a sheath flow cuvette. The sheath fluid, identical to the CE run buffer, was introduced into the cuvette hydrodynamically by keeping the inlet reservoir of the sheath buffer 1 cm higher than the outlet reservoir. The vertically polarized laser beam was focused onto a spot about 20 mm below the tip of the capillary. The angle and position of the cuvette relative to the detection optical path were adjusted so that roughly equal signals with maximum outputs from both PMTs were achieved. The values of fluorescence anisotropy (A) were calculated according to (Shimura, et al., 1994; Schultz, et al., 1993; Lakowicz 1983).

$$A = (I_v - I_h)/(I_v + 2I_h) \tag{2}$$

where $I_v$ and $I_h$ are the fluorescence intensities of vertically and horizontally polarized components, respectively.

The values of fluorescence polarization, P, were calculated according to (Lakowicz 1983; Perrin 1926; Weber, 1953; Dandliker, et al. 1970)

$$P = (I_v - GI_h)/(I_v + GI_h) \tag{3}$$

where $I_v$ and $I_h$ are the fluorescence intensities of the vertically and horizontally polarized components, respectively; G is an empirical constant that corrects for the polarization bias introduced by the optics and the detection system. The G value was determined as the intensity ratio of vertical to horizontal polarization components of fluorescein. For a well-balanced system, the polarization bias is relatively small (G=0.98-1.0) and therefore, is negligible.

It is possible to have unequal transmission of the two orthogonal polarizations through the emission optical trains and, therefore, unequal sensitivity of the PMT detectors for vertical and horizontal polarized emission. To correct for this potential bias, the PMT voltage was adjusted until the fluorescence intensities from the two PMT's (the vertically and horizontally polarized fluorescence) were identical for dilute fluorescein ($10^{-9}$ M), which is assumed to have negligible anisotropy.

In the first set of examples, laser induced fluorescence polarization (LIFP) detector was used in conjunction with capillary electrophoresis to demonstrate the utility of CE/LIFP. Changes in the electrophoretic mobility and fluorescence polarization of the fluorescent probe upon complex formation with the binding partner were measured simultaneously, thereby providing complementary information on the binding interaction. This information could not be obtained with either CE or LIFP used alone. Unless otherwise noted, the smaller molecule of a binding pair was labeled with a fluorophore such as fluorescein. The complex was formed by mixing the fluorescent substrate with the corresponding binding partner and was electrophoretically separated from the unbound substrate followed by on-line detection with LIFP. Our results showed expected increases in fluorescence polarization upon complex formation, demonstrating the usefulness of the technique in binding studies involving a wide variety of biomolecules.

For binding systems that have low affinity, dissociation may take place during separation. We overcame this problem by including the binding reagents in the CE separation buffer to stabilize the complex as demonstrated in system in DNA-protein binding studies. A fluorescently labeled oligonucleotide or SSB protein was used as a probe and the binding interactions with its partner were studied in either of two formats, depending on the stability of the complexes formed. For weak binding interactions, the binding partner was included in running buffer to stabilize the complexes during CE separation. The electrophoretic mobility and fluorescence anisotropy of the fluorescent probe were measured as a function of the concentration of its binding partner in the running buffer. Both the electrophoretic mobility and fluorescence anisotropy were used to determine the binding constants and cooperativity. For high affinity interactions, mixtures containing the fluorescent probe and its binding partner at varying ratios were incubated prior to separation. The complexes formed off-column were then separated by CE with a running buffer free of the binding components. The electrophoretic mobility and fluorescence anisotropy measurements were used for the identification of the complexes and for the study of binding stoichiometry.

Materials and Reagents. Disodium fluorescein of purified grade was obtained from Fisher Scientific (Fair Lawn, N.J.) and was used for instrument alignment. Fluorescein isothiocyanate (FITC) isomer I, L-tryptophan, staphylococcal enterotoxin A (SEA), polyclonal (rabbit) antibody to SEA, SSB protein, d(pT)$_{18}$, single-stranded M13mp8 phage DNA and FPIA (fluorescence polarization immunoassay) dilution buffer (pH 7.4) containing phosphate, bovine protein and sodium azide, were obtained from Sigma (St. Louis, Mo.).

Fluorescein-dUTP was obtained from Molecular Probes (Eugene, Oreg.). A 5'-oligolabeling kit containing T4 polynucleotide kinase, ATPS and 5-iodoacetamidofluorescein (IAF) was obtained from Amersham Pharmacia Biotech (Buckinghamshire, England).

Fluorescein labeled oligonucleotides 11-mer (5'-CGC-GATACGCC-3'; SEQ ID NO:1) and 37-mer (5'-CCT-TAAGCTTCCTCAACCACTTACCATACTCGAGATT-3'; SEQ ID NO:2) were provided by J. Lee of Cross Cancer Institute and T. Carnelley of Department of Public Health Sciences, University of Alberta.

The fluorescein labeled vancomycin and polyclonal (sheep) antibody to vancomycin were from a Sigma diagnostics reagent set. The actual compositions and concentrations of these solutions were not available. The trp repressor protein, trp operator DNA and trp binding buffer (pH 7.6) were obtained from PanVera (Madison, Wis.) as a trp repressor-DNA binding kit. The trp operator was a 5'-fluorescein labeled, 25 base pair, oligonucleotide with sequence:

```
(5'-ATCGAACTAGTTAACTAGTACGCAA-3')

(3'-TAGCTTGATCAATTGATCATGCGTT-5')
```

Fluorescent Labeling of SEA. SEA was labeled with FITC and the extent of modification was estimated according to the methods described by Brinkley, et al., 1992. A 10-fold molar excess of FITC was added to a solution of SEA (0.1 mg/mL) in 25 mM Na$_2$B$_4$O$_7$ (pH 9.1). The reaction was allowed to proceed for 1 h at room temperature and then terminated by adding excess of hydroxylamine. The fluorescently labeled SEA was transferred into a disposable dialyzer tube (Spectra/Por CE Sterile DispoDialyzer, molecular weight cut-off 10,000 Da) and purified by dialysis against 10 mM sodium phosphate buffer (pH 7.4) at 4° C. for 2 days. The degree of fluorescent labeling was determined by analyzing the fluorescently labeled SEA and the free dye in 25 mM Na$_2$B$_4$O$_7$ (pH 9.1) using a Hewlett-Packard (Palo Alto, Calif.) Model 1040A diode array detector. A Gilson (Villies le Bel, France) Model 307 HPLC pump was used to introduce the sample solution. The molar ratio (R) of the fluorophore to SEA protein was calculated according to the following equation:

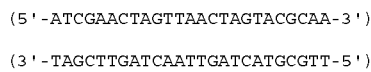

$$R = A_{490,p} e_p / [A_{277,p} - A_{490,p}(A_{277,d}/A_{490,d})] e_d \quad (4)$$

where $A_{277,p}$ and $A_{490,p}$ are the absorbance of fluorescently labeled SEA protein at 277 and 490 nm; $A_{277,d}$ and $A_{490,d}$ are the absorbance of the free dye at 270 and 490 nm; $e_p$ and $e_d$ are the extinction coefficients of SEA at 277 nm and the free dye at 490 nm, respectively.

Fluorescent Labeling of SSB protein and d(pT)$_{18}$. The SSB protein was labeled with FITC and the extent of modification was estimated according to the methods described by Brinkley, et al., 1992. A 10-fold molar excess of the dye was added to a solution of the SSB protein (1.4 μg/mL) in 25 mM Na$_2$B$_4$O$_7$ (pH 9.1). The reaction was allowed to proceed for 1 h at room temperature and then stopped by adding excess of hydroxylamine. The FITC-labeled protein was purified using a prepacked bio-spin column (Bio-Gel P-6, Bio-Rad, Hercules, Calif.). The absorbance of FITC (280 nm) and FITC-SSB (490 nm) in 25 mM Na$_2$B$_4$O$_7$ (pH 9.1) was measured using a Hewlett-Packard (Palo Alto, Calif.) Model 1040A diode array detector equipped with a Gilson (Villies le Bel, France) Model 307 HPLC pump. The molar ratio of the fluorophore to protein was calculated from the absorbance measurements using the following extinction coefficients: FITC (Fey, et al., 1984), $e_{490}$=73000 cm$^{-1}$ M$^{-1}$; and SSB (Thompson, et al., 1986), $e_{280}$=120 000 cm$^{-1}$ M$^{-1}$. Absorbance of FITC at 280 nm was corrected for in the calculation of the molar ratio of FITC to protein. The labeling of d(pT)$_{18}$ at the 5'-end with 5-iodoacetamidofluorescein was accomplished by following a protocol provided by Amersham.

Formation of the Complexes. Various volumes (0, 2, 4, 6, 8 mL) of antibody solution from a test kit for vancomycin were mixed with 10 mL aliquots of fluorescein-labeled vancomycin solution in 0.5 mL microcentrifuge tubes. FPIA dilution buffer was added to each tube to a final volume to 200 mL. The tubes were vortexed for 30 s and the mixture was allowed to incubate at room temperature for 15 min. Binding studies for SEA-antibody and trp repressor-operator systems were conducted similarly, with appropriate amounts of the binding partners. The samples were analyzed by CE/LIFP.

For weak interactions, protein-DNA complexes were formed on-column with excess amounts of the protein. Buffer solutions containing various concentrations of the SSB protein or oligonucleotide were used as CE running buffers. The fluorescently labeled DNA was injected into the capillary for CE/LIFP analysis. For strong interactions, protein-DNA complexes were formed off-column. Various volumes (0, 2.5, 5.0, 10, 15 mL) of the M13 phage DNA solution (43 nM) were mixed with 1.0-mL aliquots of FITC-SSB protein solution (12.5 mM) in 0.5-mL microcentrifuge tubes. FPIA dilution buffer was added to each tube to a final volume of 50 mL. The tubes were vortexed for 30 s and the mixtures incubated at room temperature for at least 15 min prior to CE/LIFP analysis.

Example 1

Peptide-Protein Interaction. Binding of vancomycin to its antibody was chosen as an example because of the therapeutic importance of vancomycin and because of the availability of its antibody as an affinity agent. Vancomycin is a water soluble, tricyclic glycopeptide and is strongly bound to its antibody in solution as has been demonstrated in a homogenous immunoassay (Schenzer, et al., 1983).

The complex, formed as described above, and the unbound vancomycin can be resolved by CE and can be readily identified based on their differential fluorescence polarization values. Two electropherograms were obtained from a single CE separation of a sample containing fluorescein-labeled vancomycin and anti-vancomycin antibody and are shown in FIG. 1. Both vertically ($I_v$) and horizontally ($I_h$) polarized fluorescence components were measured simultaneously. Fluorescein was added as a reference compound to correct for any possible polarization bias of the instrument. The fluorescein-labeled vancomycin and the fluorescein dye rotate rapidly in solution and exhibit little fluorescence polarization. Thus, the fluorescence intensities corresponding to the two polarized components are nearly equal. The binding of vancomycin to its antibody results in a substantial increase in the molecular size and a slower rotation of the molecule. The complex exhibits significant fluorescence polarization. The intensity of the vertically polarized fluorescence ($I_v$) was significantly higher than that of the horizontal component ($I_h$) for the complex. The same trend was observed with the complex formed at various vancomycin to antibody ratios. A mean fluorescence polarization was found to be 0.28±0.02. This value represents the intrinsic polarization of the complex, which depends on rotational diffusion of the molecule but is independent of the amounts of the drug and antibody added.

The increase of fluorescence polarization upon complex formation can be expected from the fluorescence polarization principle (Lakowicz 1983; Perrin 1926; Weber, 1953; Dandliker, et al. 1970). A fluorescent molecule, when excited by a polarized light, emits fluorescence with its polarization (P) controlled by rotational correlation time (f) and fluorescence lifetime (t) as shown by the Perrin equation (Perrin, 1926)

$$(1/P - 1/3) = (1/P_0 - 1/3)(1 + t/f) \quad (5)$$

where $P_0$ is the intrinsic polarization in the absence of rotational diffusion. When the rotational correlation time is small relative to the fluorescence lifetime, the fluorescence is depolarized. When the fluorescence lifetime is constant for a given fluorophore (e.g., 4 ns for fluorescein), an increase in polarization may be observed with increasing rotational correlation time. The rotational correlation time can be estimated according to the Debye-Stokes-Einstein equation (Gottfried, et al., 1999)

$$f = Mh(v+h)/RT \quad (6)$$

where M is the mass of the molecule, h is the viscosity of the solution, v is the specific volume of the molecule, h is the degree of hydration, T is the absolute temperature, and R is the ideal gas constant. Using a typical specific volume (v) of 0.735 cm$^3$/g and a typical value of hydration (h=0.2 cm$^3$/g) (Gottfried, et al., 1999), we estimated the rotational correlation time of vancomycin (0.7 ns) and its complex with the antibody (58 ns). The reduced rotational diffusion of vancomycin when bound to the antibody resulted in an increase in fluorescence polarization from 0.08 for the free vancomycin (1838 Da) to 0.28 for the antibody-bound vancomycin (~152,000 Da). The molecular weight, the estimated rotational correlation time and the observed fluorescence polarization are summarized in Table 1.

TABLE 1

Molecular weight, estimated rotational correlation time and observed fluorescence polarization of FITC labeled substrates and their protein complexes

| Substrate and Complex | Molecular Weight (Da) | Estimated Rotational Correlation Time (ns)[a] | Observed Fluorescence Polarization |
|---|---|---|---|
| FITC labeled substrates | | | |
| Vancomycin | 1,838 | 0.7 | 0.08 ± 0.02 |
| Trp Operator | 15,000 | 5.8 | 0.11 ± 0.02 |
| SEA | 28,000 | 11 | 0.14 ± 0.02 |

TABLE 1-continued

Molecular weight, estimated rotational correlation time and observed fluorescence polarization of FITC labeled substrates and their protein complexes

| Substrate and Complex | Molecular Weight (Da) | Estimated Rotational Correlation Time (ns)[a] | Observed Fluorescence Polarization |
|---|---|---|---|
| Complexes | | | |
| Vancomycin-Antibody | 152,000 | 58 | 0.28 ± 0.02 |
| Trp Operator-Repressor | 30,000 | 12 | 0.25 ± 0.02 |
| SEA-Antibody | 180,000 | 69 | 0.14 ± 0.02 |

[a]Calculated from eq (4), with T = 293 K, v = 0.735 cm$^3$/g and h = 0.2 cm$^3$/g, (see ref 15).

As an intrinsic property of a molecule, the characteristic fluorescence polarization provides evidence for the binding of the substrate to its antibody without the need of tedious titration procedures, thereby promising considerable savings on time and reagents. This feature makes the CE/LIFP approach particularly suitable for applications such as screening specific monoclonal antibodies where the speed and convenience are the major concerns when choosing a screening method (Barret, 1994).

Example 2

Protein-Protein Interaction. Binding of SEA to its antibody was studied with an intention of developing CE based immunoassays for this natural toxin. SEA has been known for many years to cause food poisoning (Marrack, et al., 1990) and, therefore, it is of considerable public health interest to develop rapid and sensitive analytical methods. Radioimmunoassays and enzyme-linked immunosorbent assays for this toxin have been described in the literature (Johnson, et al., 1973; Fey, et al., 1984; Thompson, et al., 1986).

Experiments were run to characterize the FITC labeled SEA and to examine the formation and stability of its complex with the corresponding antibody. Using equation (1) and literature values of extinction coefficients for the dye ($e_d$=73,000 cm$^{-1}$ M$^{-1}$) and the protein ($e_p$=40,900 cm$^{-1}$ M$^{-1}$), (Haugland, 1996; Schantz, et al., 1972) we estimated the molar ratio of the dye to the protein to be 5.9±0.3 for the labeled SEA.

Fluorescently labeled SEA exhibits an appreciable polarization (0.14), making it readily identifiable even in the presence of the residual dyes. This finding suggests that the CE/LIFP may be used to monitor the progress of labeling reactions and to verify the purity of the reaction products. The broadness of the peak is attributed to the heterogeneity of the protein (Schantz, et al., 1972) as well as to the presence of multiply labeled products (Craig, et al., 1998).

The electropherograms from a CE/LIFP analysis of a mixture of FITC-SEA and its antibody show a new peak attributable to the complex between fluorescently labeled SEA and its antibody. The complex exhibited measurable fluorescence polarization (0.14) as seen with the free SEA. However, there was no net increase of polarization upon complex formation. This is not surprising given the relatively high molecular weight of SEA itself (28,000 Da). In an aqueous solution at room temperature, the rotational correlation time (f) of SEA is estimated using equation (6) to be approximately 11 ns, which is about 2.5 lifetimes of fluorescein (t, less than 4 ns). With such a long rotational correlation time, the t/f term (<0.4) in equation (5) contributes little to the observed fluorescence polarization (P). The polarization may approach to $P_0$, the intrinsic value for the molecule because it is known that fluorescence polarization generally approaches saturation with molecular weight beyond 20,000 Da (Guo, et al., 1998). As a result, further increase in correlation time due to the binding of antibody did not lead to any significant increase in polarization. The polarization of 0.14 for the complex is well below the theoretical limit of 0.5, indicating that local rotation of the fluorophore may occur within the SEA molecule.

Because of no increase in polarization noted in this case, additional evidence is needed to confirm the complex formation, which can be obtained by titrating a fixed amount of FITC-SEA with varying amounts of the antibody. As expected, the complex peak increases at the expense of the unbound SEA peak (Wan, et al., 1999)

Example 3

Protein-DNA interaction. The interaction between trp operator (DNA) and trp repressor protein of *Escherichia coli* serves as a well-characterized system for gene expression and regulation (Crawford, et al., 1980). In the presence of tryptophan, the repressor protein binds with high affinity to the operator sequence found within the promoter region of the trpEDCBA operon and represses transcription of those genes whose protein products are responsible for the synthesis of tryptophan. In the absence of tryptophan, trp repressor is inactive and the trp operon is expressed, resulting in the biosynthesis of tryptophan. The binding of the trp operator to trp repressor has been studied extensively (Carey, 1988; Otwinowski, et al., 1988; Lawson, et al., 1988; LeTilly, et al., 1993; Zhang, et al., 1994; Stebbins, et al., 1996).

Two formats were used to explore the potential of CE-LIFP in the study of DNA-protein interactions in the trp operator (DNA) and trp repressor protein system. In the first format, the affinity complex was formed dynamically in the separation capillary and maintained at equilibrium with the free protein during the electrophoresis. In the second format, the complex was preformed by incubation and then separated from the unbound protein molecule.

The electropherograms of fluorescently labeled trp operator oligonucleotide obtained with and without the trp repressor protein in the running buffer were compared. The $I_v$ and $I_h$, representing vertically and horizontally polarized fluorescence, respectively were measured. In the presence of the trp repressor, a tailed peak with migration time of 4.6 min was observed. This peak corresponds to the complex formed between the trp operator and trp repressor judging from the fluorescence polarization that increased from 0.11 (without the trp repressor in the running buffer) to 0.25 (with the inclusion of the trp repressor in the running buffer).

It is noted that fluorescently labeled DNA displays multiple peaks in both cases and that these peaks do not disappear even in the presence of excess trp repressor. The persistence of the multiple peaks suggests the presence of multiple DNA structures (Stebbins, M. A, et al., 1996; Hamdan, et al., 1998), some of which are not recognized by the repressor protein. Experiments have established the dynamic formation of the DNA-protein complex (Wan, et al., 1999).

Example 4

SSB protein/ssDNA. The SSB protein plays an important role in the DNA replication, recombination and repair proces (Bandyopadhyay, et al., 1978; Krauss, G., et al., 1981; Chase, et al., 1986; Lohman, et al., 1994) although mechanisms for its functions in these processes have not yet been elucidated. The SSB protein exists as a tetramer in solution with a subunit weight of about 20 000. It binds cooperatively to single-stranded DNA (approximately 32-60 nucleotides per protein), keeping the DNA in an extended configuration and protecting it from nuclease digestion. The results shown in the SSB/DNA binding experiments demonstrate the resolving power and identification capabilities of CE/LIFP in these systems.

CE/LIFP may be used in binding studies through the measurement of changes of either electrophoretic mobility or fluorescence anisotropy of a binding component upon affinity interactions. Usually, the binding component of lower molecular weight is used as a probe so as to induce greater mobility or anisotropy changes upon binding. In this example, both fluorescently labeled DNA fragments and binding protein were used as probes for the study of protein-DNA interactions.

In this example, a fluorescein labeled 11-mer (F-11-mer) was evaluated as a probe for examining its binding with the SSB protein. Electropherograms of F-11-mer in the absence and presence of the SSB protein in the running buffer were run and the vertical ($I_v$) and horizontal ($I_h$) components of fluorescence were measured simultaneously for each. Fluorescein labeled dUTP (F-dUTP) was used as a reference compound to correct for possible fluctuations in electroosmotic flow and unequal detection sensitivity between the two detection channels of the instrument. In the absence of the binding protein, the fluorescent probe has an electrophoretic mobility of $m=3.99 \times 10^{-4}$ cm$^2$ V$^{-1}$ s$^{-1}$ and a fluorescence anisotropy of $A=0.05$. In the presence of 0.7 mM of the SSB protein in the running buffer, the electrophoretic mobility of the oligonucleotide probe is reduced to $1.93 \times 10^{-4}$ cm$^2$ V$^{-1}$ s$^{-1}$ whereas the anisotropy is increased to 0.25. The decrease in electrophoretic mobility and increase in anisotropy are due to the binding of the F-11-mer with the SSB protein. In contrast, the mobility and anisotropy of F-dUTP are essentially unchanged, consistent with the fact that the SSB protein has very low binding affinity for the mononucleotide.

The electrophoretic mobility and anisotropy changes observed in the experiments arise from the effects of the binding protein on the molecular motion of the probe. In the absence of the binding protein, the fluorescently labeled oligonucleotide probe migrates with a mobility similar to that of F-dUTP in the free zone electrophoresis mode. It has a low fluorescence anisotropy because of its small molecular size (MW 4 000) and random motion in solution. When bound to the SSB protein (MW 80 000), the size of the fluorescent molecule is markedly increased, resulting in a slower molecular motion in the solution. Therefore, it is not surprising that binding of the SSB protein to the oligonucleotide probe gives rise to a marked increase in anisotropy. The mobility and anisotropy of the complex approach to those of the binding protein ($m=1.07 \times 10^{-4}$ cm$^2$ V$^{-1}$ s$^{-1}$ and $A=0.23$ for FITC-SSB. While the electrophoretic mobility of a compound is proportional to its charge to mass ratio, (Chu, et al., 1995; Baker, 1995) the fluorescence anisotropy is mainly determined by its molecular size, shape, and fluorescence lifetime (Lakowicz, 1999).

The mobility and anisotropy of the F-11-mer were measured with the running buffer containing various concentrations of the SSB protein. Nanoliter amounts of the F-11-mer ($10^{-9}$ M) were injected into the capillary that was filled with the running buffer containing $10^{-7}$-$10^{-6}$ M SSB protein. Thus, the concentration of the binding protein in the running buffer was in large excess and was not affected significantly by its binding with the F-11-mer. Under this condition, the quantitative interpretation of the binding profiles can be carried out using a standard four-parameter logistic equation (Motulsky, 1999):

$$y=(a+bK^n x^n)/(1+K^n x^n) \tag{7}$$

where y is the observed response such as electrophoretic mobility or fluorescence anisotropy of the oligonucleotide probe at a given concentration of the binding protein, x; K is the apparent binding constant; a and b are the responses of the free and bound probe, respectively; and superscript n is the Hill coefficient describing the steepness of the curve. The experimental data were fitted to the above equation using nonlinear regression analysis (SigmaPlot, version 4, SPSS Inc.). Binding constant (K) measurements based on mobility and anisotropy of the F-11-mer were similar, which were approximately $4.4 \times 10^6$ M$^{-1}$ and $5 \times 10^6$ M$^{-1}$, respectively. These values are comparable to previous measurements by other methods. For example, Molineux (Molineux, et al, 1975) reported that SSB has an affinity of about $2 \times 10^6$ M$^{-1}$ for d(pT)$_8$ and Krauss (Krauss, et al, 1981) reported an affinity of $1.4 \times 10^6$ M$^{-1}$ for d(pT)$_{16}$ using fluorescence quenching methods. Binding constants and fitting parameters from nonlinear regression analysis are summarized in Table 1.

Furthermore, binding interactions involving protein-DNA complexes that differ in stoichiometry can be accomplished with this instrumentation. Fluorescein labeled 37-mer (F-37-mer) was chosen as a DNA probe since its complexes with the SSB protein are of higher stability, allowing examination of a distribution of different species in the binding interactions. Electropherograms of F-37-mer with the absence and presence of the SSB protein in the CE running buffer were collected. Changes in electrophoretic mobility and fluorescence anisotropy upon formation of complexes between F-37-mer and SSB protein are observed as expected. It is noted that the initial single peak of F-37-mer was split into two when bound to the SSB protein. Both complex peaks display strong fluorescence isotropy (A=0.23). These are likely 2:1 (peak 2) and 1:1 (peak 1) protein-DNA complexes. For the 1:1 binding interaction, variations of the m and A values for the F-37-mer with the binding protein concentration were compared, from which the apparent binding constants were obtained. Again, both mobility and anisotropy measurements gave very similar results, with binding constants of approximately $2 \times 10^7$ M$^{-1}$ (see Table 1). This is approximately 5-fold increase in binding affinity of SSB for the 37-mer compared to its binding with the 11-mer. This is consistent with the contribution of cooperativity to the binding strength. The SSB protein is a tetramer and the number of the binding sites of the SSB protein varies with the length of the oligonucleotides because each of the four subunits of the protein covers 6-8 nucleotides (Krauss, et al, 1981; Chase, et al., 1986). While one subunit may bind to the 11-mer, all the four subunits of the SSB tetramer could bind to the 37-mer, resulting in the corresponding increase in binding constant. Because the two complex species were not well resolved particularly at low protein concentrations, there was a relatively large uncertainty associated with mobility and anisotropy measurements for the 2:1 complex. Consequently, we were unable to precisely determine the corresponding binding constant for the 2:1 complex.

Example 5

Fluorescein Labeled DNA Binding Protein as a Probe. Fluorescently labeled DNA oligonucleotides have exclusively been used as probes in the analysis of protein-DNA interactions by gel retardation, CE or FP techniques. However, many bioanalytical applications require the use of a fluorescently labeled binding protein for its ability to recognize and bind to specific structures of DNA. In this example, FITC-labeled SSB protein interacts with a synthetic oligonucleotide and a single-strand DNA. The FITC-labeled SSB protein was prepared as described in the experimental section and the dye to protein molar ratio was 5.3. In a solution of 25 mM disodium tetraborate with pH 9.1, the labeled SSB protein displayed an electrophoretic mobility of $1.07 \times 10^{-4}$ cm$^2$ V$^{-1}$ s$^{-1}$ and a fluorescence anisotropy of 0.23.

Electropherograms of FITC-SSB protein were obtained with running buffers containing varying amounts of oligonucleotide, d(pT)$_{18}$. Both vertically and horizontally polarized fluorescence emissions were acquired simultaneously. There was only a slight increase in fluorescence anisotropy (DA >>0.02) of the protein probe upon binding to the oligonucleotide. This is in accordance with the fact that fluorescence anisotropy of a probe generally approaches saturation when the probes molecular weight exceeds 20000 (Lakowicz, 1999; Wan, et al., 1999; Guo, et al., 1998).

It is noted that formation of the complex gives rise to some significant changes in the mobility and peak shape of the FITC-labeled SSB protein. As the concentration of d(pT)$_{18}$ in the running buffer increases, the electrophoretic mobility of the SSB protein increases with the peak becoming increasingly dispersed. The mobility increase of the low mobility species (the FITC-SSB protein, m=$1.07 \times 10^{-4}$ cm$^2$ V$^{-1}$ s$^{-1}$) is due to its binding to a high mobility DNA (m=$2.19 \times 10^{-4}$ cm$^2$ V$^{-1}$ s$^{-1}$ for fluorescein labeled d(pT)$_{18}$). The peak broadening suggests that the formation of multiple protein-DNA complexes is possible in the presence of increasing amount of DNA. A single protein molecule may bind several DNA molecules in the presence of excess DNA. The complexes of varying protein to DNA ratios co-migrate in the separation capillary as a broad band. To clarify this point, we chose a DNA fragment much longer than d(pT)$_{18}$ to form stable complexes with the SSB protein. Because of increased stability, the multiple complexes formed off-column can be separated without the need for adding the binding partner to the running buffer.

Example 6

Detection of labeled protein binding to ssDNA. In the following embodiment, single-stranded M13 mp8 phage DNA (7 229 bases) was selected as a binding partner for the labeled SSB protein. Varying amounts of the phage DNA were incubated with a series of binding solutions containing a fixed amount of the FITC-labeled SSB protein. The mixtures were then analyzed by CE/LIFP with a running buffer free of the binding components. Separations of FITC-SSB protein and its complexes with the DNA at various molar ratios of DNA to protein show that as the amount of DNA in the reaction mixture increases, new peaks emerge and become increasingly retarded and broadened. The broad and multiple peaks with increasing migration times showed strong fluorescence anisotropy (A=0.25), indicating the presence of multiple protein-DNA complexes. Three major peaks with increasing mobilities (peak 2, $2.16 \times 10^{-4}$ cm$^2$ V$^{-1}$ s$^{-1}$; peak 3, $2.66 \times 10^{-4}$ cm$^2$ V$^{-1}$ s$^{-1}$; and peak 4, $3.16 \times 10^{-4}$ cm$^2$ V$^{-1}$ s$^{-1}$) corresponded to the complexes with increasing DNA to protein ratios.

In the absence of the DNA, peak 1 corresponds to the SSB protein probe which has a m=$1.07 \times 10^{-4}$ cm$^2$ V$^{-1}$ s$^{-1}$. Addition of the DNA to the protein (with DNA-to-protein ratio of 0.008 and 0.016) causes a decrease in peak 1 and the appearance of peak 2 (m=$2.16 \times 10^{-4}$ cm$^2$ V$^{-1}$ s$^{-1}$), indicating the formation of DNA-protein complex. With further increase of DNA-to-protein ratio, the mobilities of the complexes (2.66× $10^{-4}$ cm$^2$ V$^{-1}$ s$^{-1}$ for peak 3; and 3.16×10$^{-4}$ cm$^2$ V$^{-1}$ s$^{-1}$ for peak 4) shift towards that of the DNA (m=3.50×10$^{-4}$ cm$^2$ V$^{-1}$ s$^{-1}$).[27] Because the amount of the protein was fixed in this series of experiments, increasing amounts of DNA in the reaction mixture favor the formation of complexes of increasing DNA:protein ratio. This example demonstrates an application of CE/LIFP to study multiple-complexes.

Section B: Examples 7-10

Complex Formation Between HIV-RT and Aptamers

In the next few examples the detection of human immunodeficiency virus type 1 reverse transcriptase was accomplished using aptamers as probes in affinity capillary electrophoresis and laser induced fluorescence polarization. CE determination of HIV-1 RT using a noncompetitive affinity assay has several advantages in terms of vastly decreasing analysis time and involves much simpler chemical procedures. A fluorescently-labeled aptamer such as RT 12 or RT 26 eliminates the need for the use of radio-labeled materials, and provides the first direct assay for HIV-1 RT. Since the aptamers were evolved to bind selectively to HIV-1 RT, interferences from RTs of other species was eliminated or greatly attenuated. Used in conjunction with other laboratory procedures correlating HIV-1 RT activity to viral loads, the assay could prove useful in the determination of HIV-1 viral load.

Apparatus: The CE/LIF instrument used in this work is the same as described above except that a 543.5 nm green He—Ne laser (Melles Griot, Irvine, Calif., USA) with a 5 mW maximum out put was used as the excitation source.

Reagents: All solutions were prepared using 18.2 MW distilled, deionized water (DDW) from a Milli-Q Gradient 10 Water System (Millipore, Nepean, Canada). Tris-borate-EDTA (TBE) (0.089 M tris, 0.089 M boric acid, 0.0025M EDTA, pH 8.3), tris-glycine (0.025 M tris, 0.192 M glycine, pH 8.3) and disodium tetraborate buffers (0.1 M, pH 9.1) were prepared using reagent-grade materials and diluted to desired concentrations with DDW prior to being filtered through a 0.22 μm filter to remove particulate matter. The RT 12 aptamer (5'-ATCTACTGGATTAGCGATACTCGATT-AGGTCCCCTGCCGCTAAACCATACCGCG GTAACT-TGAGCAAAATCACCACTGCAGGGG-3'; SEQ ID NO:3) and the RT 26 aptamer (5'-ATCCGCCTGATTAGC-GATACTTACGTGAGCGTGCTGTC-CCCTAAAGGTGATACG TCACTTGAGCAAAATCAC-CTGCAGGGG-3'; SEQ ID NO:4) were labeled with 5'-FAM (5'-carboxyfluorescein) at the University Core DNA Services, University of Calgary, Canada. HIV-1 RT was obtained from Worthington Biochemicals (Lakewood, N.J.). RTs from the enhanced avian myeloblastosis virus (AMV) and the Moloney murine leukemia virus (MMLV) were obtained from Sigma (Mississauga, Canada). Cell culture media (RPMI with 10% fetal bovine serum (FBS)) was obtained from the Cross Cancer Institute at the University of Alberta.

Capillary Electrophoresis/Laser-Induced Fluorescence: Uncoated fused silica capillaries (20 μm I.D., 150 μm O.D.) were cut to a length of 40 cm and inserted into the sheath flow cuvette where the laser beam was focused. Samples were injected for 5 s at a voltage of 15 kV (375 V/cm), and electrophoresis was carried out at a running voltage of 20 kV (500 V/cm). The running buffer utilized for all experiments was 1× tris glycine. The laser power was set at 4 mW throughout. Periodically, the capillaries were treated by running 0.1 M NaOH through the system at an running voltage of about 100 V/cm for 30 mintues, followed by the running buffer (1× tris glycine) at 500 V/cm, to remove protein material adsorbed on the capillary wall.

Affinity Complex Formation: The RT 12 aptamer and RT 26 aptamer were received in 0.020 μg and 0.040 μg quantities, respectively. These were diluted to 60 μL in 1×TBE in 600 μL microcentrifuge tubes and stored in a freezer at 20° C. when not in use, as were the RTs of HIV-1, AMV and MMLV. Stock solutions of 80 nM for the RT 12 aptamer and 170 nM for the RT 26 aptamer were prepared in 1×TBE in 600 μL microcentrifuge tubes. A 1000 nM stock solution of HIV-1 RT was similarly prepared in DDW. Complex formation was carried out in an incubation buffer of 1×TBE. The desired concentration of aptamer and protein was obtained by pipeting the appropriate volumes of aptamer and protein stock solutions into a 60 μL volume in 600 μL microcentrifuge tubes. The tubes were then vortexed for 30 s and put on ice for about 5 minutes prior to sample injection into the capillary. All stock solutions were stored at 20° C. when not in use and all samples were kept on ice during the course of experimentation.

Interference Studies: To determine the degree to which the aptamers would bind with RTs from AMV and MMLV, experiments were conducted in which complex formation experiments, as described above, were undertaken with AMV and MMLV RTs substituted for HIV-1 RT. Furthermore, complex formation experiments were conducted with RTs of HIV-1, AMV and MMLV mixed together, with the AMV and MMLV RTs at the same or higher concentration than HIV-1 RT. To determine the degree to which matrix effects from cell culture media would interfere with complex formation, aliquots of RPMI containing 10% FBS were added to samples containing both HIV-1 RT and aptamer, as well as aptamer alone.

Example 7

Detection of Affinity Complex Formation after CE Separation. The affinity complex was formed by adding increasing concentrations of aptamer to a fixed concentration of HIV-1 RT (50 nM). In the absence of HIV-1 RT, the aptamer peak is sharp with a migration time of around 4.2 minutes. Tailing, a characteristic of the aptamer peak, was observed even at the lowest aptamer concentrations used (1.7 nM). This most likely results from impurities in the DNA, as has been previously observed (German, et al., 1998). These DNA impurities likely contain multiple DNA structures, which cannot be recognized by the HIV-1 RT protein (Wan, et al., 1999; Stebbins, et al., 1996; Hamden, et al., 1998).

The RT-26-HIV-1 affinity complex was formed. The peak corresponding to the complex had a migration time of about 3.3 minutes and was well resolved and Gaussian in appearance. The lack of features such as bumps or shoulders suggested that the affinity complex was primarily of single stoichiometry. At concentrations of 50 nM HIV-1 RT and 17 nM RT 26, the complex peak migrated as a doublet or a shoulder appeared, indicating that RT 26 and HIV-1 RT were forming a complex of two stoichiometries. The peak area of the HIV-1 RT-aptamer affinity complex increases with increasing aptamer concentration.

Experiments were also undertaken using RT 12 at 8, 15, and 20 nM concentrations added to a solution containing a fixed concentration of 50 nM of HIV-1 RT. The results parallel those described above, in that the CE peak area of the affinity complex increased with increasing aptamer concentration. However, the RT 12-HIV-1 RT affinity complex exhibited two distinct peaks, one forming at the same migration time as the RT 26-HIV-1 RT complex, while an additional early peak formed at about 2.9 minutes. HIV-1 RT is a heterodimer of total molecular weight (120 kDa) with two sub-units of molecular weight 51 kDa and 66 kDa. Although it is possible that the dimeric forms of HIV-1 RT may be binding to different sites on the differently-structured RT 12 aptamer, a more likely explanation is that the RT 12 is being incorporated into the affinity complex in such a way as to produce a complex of two different stoichiometries (Wan, et al., 1999). Later experiments, in which the RT 12-HIV-1 RT affinity complex was observed to migrate as a single peak, confirm the belief that an affinity complex of different stoichiometries was formed in these experiments. Because of the higher binding constant of the RT 26 aptamer (81-mer), it was chosen for all further work.

Example 8

Use of CE/LIFP to create Calibration Curves: Calibration curves for HIV-1 RT were constructed using aptamer concentrations of 17 nM and 60 nM, preferebly, 17 nM of the RT 26 aptamer. The RT 26 probe peak area decreases with increasing HIV-1 RT concentration, reaching a limiting value at 100 nM and disappearing completely at 800 nM of HIV-1 RT. That the aptamer was completely incorporated into the affinity complex indicates the aptamer was at its preferred orientation in the TBE incubation buffer, without the need for heat denaturing and the presence of $Mg^{2+}$ salts, as was found in another assay in which DNA aptamers were used to bind IgE and thrombin (German, et al., 1998). Most sample solutions were stable for about two weeks if immediately frozen after use, after which both the probe and affinity complex peak areas were significantly diminished. At HIV-1 RT concentrations of 7 nM or lower, it was necessary to perform experiments within 30-40 minutes because aptamer and complex peak area began to deteriorate. Because of practical considerations such as these, calibration curve samples were prepared sequentially, and samples were prepared fresh daily.

The calibration curve for the bound complex showed an initial steep increase in fluorescence intensity with HIV-1 RT concentration, followed by leveling off, indicative of binding saturation, beginning at about 100 nM of HIV-1 RT. For the aptamer probe peak, this was mirrored by a similar steep loss in fluorescence intensity, followed by a leveling off at about 100 nM. It is incorporated in the affinity complex, ultimately completely, at 800 nM of HIV-1 RT. The steeply rising sections of the curves were then investigated to determine analytical utility. The linear dynamic range for both probe and complex peaks extends to 50 nM of HIV-1 RT. In the case of the aptamer probe, least-squares linear regression provides a best-fit line having a correlation coefficient ($r^2$) of 0.985 and a slope of 0.612, whereas the same fit to the bound complex provided an $r^2$ value of 0.986 and a slope of −0.938. Relative standard deviations range from a high of 7.1% to majority of 1.9%-2.5% for both probe and complex peaks.

Example 9

Use of CE/LIFP in Specificity determination: Experiments were performed in which all or some of the RTs were added together with HIV-1 RT and 17 nM of RT 26 aptamer. AMV RT is present at a concentration comparable to that of HIV-1 RT, whereas, MMLV RT was an order of magnitude more concentrated and was increased to over two orders of magnitude above that of HIV-1 RT. The peak areas as measured by CE of the unbound aptamer did not decrease, remaining essentially identical to that in the presence of HIV-1 RT alone. These results indicate that the presence of other RT proteins, such as AMV-RT and MMLV-RT, does not affect the determination of HIV-1 RT.

The RTs of AMV and MMLV can be shown not to cross-react with the aptamer and to be specific for HIV-1 RT. Using high concentrations of RT (4-4000 units/µL) and aptamer probe (140 nM), AMV-RT concentrations of 4 units/µL, and MMLV-RT concentrations of 4000 units/µL, The peak area of the unbound aptamer as measured by CE is essentially the same in the absence and presence of AMV-RT and MMLV-RT.

Example 10

Use of CE/LIFP to show Effects of Sample Matrix: Electropherograms from the analysis of mixtures containing 20 nM HIV-1 RT and 17 nM RT 26 aptamer in TBE buffer, in RPMI cell culture medium and in 100-fold dilute culture medium were measured. Undiluted culture medium clearly affected the formation and CE/LIF analysis of the complex. This is not surprising because the RPMI culture medium was supplemented with 10% FBS. This protein is known to affect HIV-1 RT (Lee, et al., 1987). When the cell culture medium was diluted 100-fold, the matrix interference on the complex formation and CE/LIF analysis was minimal. The analysis of mixtures of the RT 26 aptamer and HIV-1 RT in TBE buffer and in 100-fold dilute culture media show similar electropherograms.

Section C: Examples 11-21

Detection of Damaged DNA

In the next set of examples, the detection of DNA adducts of benzo[a]pyrene using immuno-electrophoresis with laser-induced fluorescence is demonstrated on the analysis of A549 cells. Benzo[a]pyrene belongs to a class of compounds called Polycyclic aromatic hydrocarbons (PAHs), which are known exhibit strong carcinogenic properties, presumably as a result of the damage that they or their metobolites cause cause to DNA. In vivo, B[a]P is converted to benzo[a]pyrene diol epoxide (BPDE). Because of the biological significance of DNA damage and repair, many techniques have been developed for the determination of DNA damage (Pfeifer, 1996).

Synthetic BPDE-DNA adduct was used as a standard probe in a competitive assay to determine the levels of BPDE-DNA adducts in a human lung carcinoma cell line exposed to BPDE. A fluorescently labeled BPDE-DNA adduct standard and a BPDE-specific antibody were added to a sample containing unknown amount of unlabeled BPDE-DNA adduct. The unlabeled BPDE-DNA adduct and the labeled BPDE-DNA adduct compete to form complexes with the antibody. CE separation of the bound and unbound adducts allows determination of the bound concentration, which in turn is related to the amount of BPDE-DNA adduct in the sample. In contrast to other methods of performing immunoassays, CE-LIF allows rapid analysis, excellent mass sensitivity and potential for automation. The popularity of this technique in immunoassays is well reflected in numerous reports, primarily for the determination of therapeutic drugs (Schulz, et al., 1995; Schmalzing, et al., 1995; Chen, et al., 1994; Evangelista, et al., 1994; Chiem, et al., 1998).

Preparation of BPDE-DNA adduct standard. BPDE powder (benzo[a]pyrene-r-7, t-8-dihydrodiol-t-9,10-epoxide (+/−) (anti) was obtained from Midwest Research Institute (Kansas City, Mo., USA. MRI 0477; Lot CSL-98-775-17-16). The BPDE powder was dissolved in dimethyl sulfoxide (DMSO) to a stock solution of 3 mM. A 16-mer oligonucleotide, 5'-CCCATTATGCATAACC-3' (SEQ ID NO:5), was treated with BPDE at a molar ratio of 1:5 (oligonucleotide: BPDE), using a protocol similar to that described by Cosman (Cosman, et al., 1990). The oligonucleotide was reconstituted in a buffer containing 20 mM phosphate/1.5% triethylamine at pH 11. To the oligonucleotide, a BPDE solution was added to a final concentration of 270 mM. The final mixture was incubated in the dark at ambient temperature overnight with gentle shaking. Purification of the BPDE-modified oligonucleotide was carried out in two separate rounds of HPLC elution using a preparative column (Phenomenex, Torrance, Calif., USA. LUNA Su C18(2); 250×10 mm 5 mm particle size). In the first round, an isocratic elution using 70% methanol and 30% of 20 mM phosphate, pH 7 was used to purify the BPDE-oligonucleotide by separating the oligonucleotides from the unreacted BPDE. The eluent containing the BPDE-oligonucleotide and the unmodified oligonucleotide was freeze dried and subjected to a second round of HPLC purification using a gradient elution of methanol/20 mM phosphate at pH 7. This purification step separates the BPDE-oligonucleotide from the unmodified oligonucleotide. The freshly purified BPDE-oligonucleotide was subjected to a standard kinase reaction to facilitate subsequent ligation to 5 other oligonucleotides to form a BPDE-DNA duplex of 90 base pairs. The BPDE-DNA duplex was gel purified using a 7.5% native polyacrylamide gel, and subsequently subjected to UV and fluorescence scanning to measure DNA concentration as well as to confirm the presence of BPDE moiety on the 90-mer.

Specific monoclonal antibodies. Monoclonal antibodies 8E11 and 5D11 were obtained from BD PharMingen (San Diego, Calif., USA). Both antibodies were derived from BALB/c mice immunized with racemic anti-BPDE modified guanosine conjugated with bovine serum albumin (Santella, et al., 1984).

Preparation of BPDE-DNA adducts from A549 cells. A human lung carcinoma cell line (A549) was incubated with BPDE to produce DNA adducts in genomic DNA. Briefly, the cell line was maintained in DMEM/F12 medium (Gibco BRL, Gaithersburg, Md., USA) supplemented with 10% fetal bovine serum. The cells were seeded at $1 \times 10^5$ cells per plate and maintained at 95% humidity and 5% $CO_2$ for 20 hours prior to the addition of BPDE. Treatment of BPDE was carried out in duplicate sets of A549 cells. Old culture media were removed from each culture plate and the cells were washed twice with phosphate buffered saline (PBS). Media containing BPDE at various concentrations (9.4, 18.8, 37.5, 75, 150, and 300 mM final concentration) were added accordingly to the designated plates. The cells were further incubated in the media containing BPDE for 2 hours. The cells were then washed with PBS prior to the addition of DNAzol lysis reagent (Gibco BRL) to facilitate cell lysis. Subsequent steps involved a standard 99.9% ice cold ethanol precipitation and a 70% cold ethanol wash to purify the genomic DNA. The final DNA pellet was dissolved in distilled deionized water (dd$H_2O$) and DNA concentration was measured at $OD_{260}$ using dd$H_2O$ as a blank.

CE-LIF Instrumentation. The instrument for capillary electrophoresis with laser induced fluorescence detection is described above, with one modification. A 543.5 nm green He—Ne laser (Melles Griot, Irvine, Calif., USA) with a 5 mW maximum output was used as the excitation source. In addition, in place of the polarizing beam splitter, a 580DF40 band-pass filter was used before the transmitted light is collected by the PMT.

CE separation. Capillary electrophoresis of the sample was performed using a 29-cm long, 20 μm i.d., 150 μm o.d. fused-silica capillary (Polymicro Technologies, Phoenix, Ariz., USA). Electrophoresis buffer was a Tris-glycine mixture containing 25 mM Tris and 192 mM glycine at pH 8.3. The injection end of the capillary was set at a positive polarity and the other end installed inside the sheath-flow cuvette was grounded. Sample introduction was performed by electrokinetic injection at 10 kV for 5 to 10 s unless otherwise indicated. Separation was performed with an electric field of 330 to 830 V/cm.

Immuno-complex of BPDE-DNA adducts. The incubation conditions were optimized for short reaction time and stable complex between the BPDE-DNA adduct and its antibody. The incubation was carried out at room temperature for 10 min in the dark. The incubation buffer was identical to the separation buffer except at half the ionic strength. The effect of buffer ionic strength on complex stability was studied by using the Tris-glycine buffer at various concentrations.

Competitive binding of BPDE-DNA adducts. Two oligonucleotides, a 16-mer and a 90-mer, were used as probes for competitive immunoassay. They each contained a single BPDE adduct in the middle and both were fluorescently labeled at a 5' end with a tetramethylrhodamine (TMR). Another adduct standard carrying an identical BPDE-DNA adduct was prepared. This adduct standard is 16 bases in length and not fluorescently labeled. This BPDE-16 mer competes with the TMR-labeled BPDE-90 mer or TMR-labeled BPDE-16 mer to form complexes with the BPDE antibody. To determine the levels of BPDE-DNA adduct in the A549 cells exposed to BPDE, the purified genomic DNA from these cells was analyzed and the adducts in the DNA competed with the TMR-labeled BPDE-90 mer standard for binding with the antibody 8E 11.

Example 11

Using CE/LIFP to determine Free solution mobility of DNA adducts. Under free zone electrophoretic conditions, DNA fragments are not separable when driven by electroosmotic flow alone because of the similar mass-to-charge ratio between DNA fragments. The immunoassay presented here makes use of an antibody to specifically form a complex with DNA adducts so that the complex can be separated from the free DNA. The antibody-bound DNA adduct migrates out first and then the unbound DNA. This migration behavior can be expected from equation (8) (Karger, et al., 1989). Eq. (8) predicts the influence of the effective charge (Q), solution viscosity (h) and the radius of an analyte (r) on electrophoretic mobility ($m_{ep}$). Both the antibody-bound and unbound DNA adducts are negatively charged. The direction of their electrophoretic mobility is opposite to that of the electroosmatic flow (EOF). The decrease in total charge-to-mass ratio after antibody binding decreases the mobility of the bound DNA adduct moving back to the injection end (positive polarity). The net result is a faster migration directed towards the detector end (direction of EOF).

$$m_{ep} = Q/6phr \quad (8)$$

Comparing the two antibodies for their affinity to the BPDE –90 mer, antibody 8E11 formed more complex than the antibody 5D11 formed. This may reflect the fact that 8E11 was raised against BPDE mononucleotides and 5D11 was raised against BPDE modified calf thymus DNA. Thus, the 5D11 might be expected to have a higher affinity for long stretches of DNA.

The longer the capillary column, the more likely that the complexes may dissociate during electrophoresis. At a capillary length of 60 cm, the amount of detectable antibody-bound DNA adducts was reduced by approximately 5-fold relative to an identical mixture separated on a 30-cm capillary. This reduction may be due to the instability of the complexes during electrophoretic separation, or may be caused by adsorption of the complexes on the capillary wall. These problems could be avoided by using a shorter column to carry out the separation without losing resolution.

Separation at high field strength also helps to improve resolution. In this Example, at a field strength of approximately 830 V/cm (25 kV for 30-cm capillary), the antibody-bound and unbound DNA adducts were baseline resolved in less than 2 minutes, with a significant improvement in separation efficiency for the antibody-bound DNA adduct. Using Tris-glycine as the separation buffer, Joule heating was not excessive at this high field strength as the current generated was very low (~2.2 mA).

Buffer strength may be varied, with the optimum separation at 0.5× Tris-glycine (12.5 mM Tris/96 mM glycine) in this Example. The plate count for the bound and unbound adducts using this buffer condition was calculated to be $6\times10^5$ and $1\times10^6$ plates per meter respectively. Incubation time and temperature were also investigated. We observed antibody binding to the DNA adduct at incubation time as short as 1 min and temperature of incubation as low as 0° C. We found that an incubation between 5 and 10 min at ambient temperature was suitable for the formation of complex and for rapid sample analysis.

To ensure that the DNA remains in its denatured form, formamide was added to the incubation buffer to prevent the complementary DNA strands from being renatured during electrophoresis. Between 2.5 and 12.5% (v/v) formamide, the ratio of the bound to unbound adducts was relatively constant. Th concentration of formamide should be kept below 82.5% (v/v).

Example 12

Using CE/LIFP in a Competitive assay. Because antibodies are bidentate, each antibody molecule is able to bind with up to two antigen molecules. One peak in the electropherogram corresponds to the complex between one antibody and one DNA adduct. A second peak corresponds to the complex of one antibody with two DNA adduct molecules. The 1:1 and 1:2 complexes between the antibody and DNA adducts are well separated, demonstrating high resolution of the CE system. A competitive assay was performed using the TMR-labeled BPDE-16 mer as a probe and the unlabeled BPDE-16 mer as a competitor. As is characteristic of competitive assays, an increase of BPDE-16 mer (unlabeled competitor) corresponds to the decrease of the complexes between the fluorescent BPDE-16 mer and the antibody.

The BPDE-90 mer that was fluorescently labeled with TMR was also used as a probe to demonstrate competitive immunoassay response with the unlabeled BPDE-16 mer. A similar competitive response was obtained, suggesting that the antibody binds to the BPDE whether it is present in the 16-mer or the 90-mer oligonucleotides.

Example 13

Using CE/LIFP to Determination of BPDE-DNA Adducts in A549 Cells

The competitive immunoassay was applied to the determination of BPDE adducts in A549 cells that were treated with various doses of BPDE. The TMR-labeled BPDE-90 mer was used as the probe and the DNA from A549 cells was heat denatured. Increasing amounts of BPDE-DNA adducts were formed as the cells were incubated with increasing concentrations of BPDE for 2 hrs. The BPDE-DNA adducts compete with the TMR labeled BPDE-90 mer probe for the antibody binding, resulting in the corresponding decrease of antibody complexes (peaks 1 and 2) of the fluorescent BPDE-90 mer. As expected one peak corresponding to the 1:1 complex between the antibody and the TMR-labeled BPDE-90 mer was observed. A second peak attributed to the 1:2 complex of antibody with the TMR-labeled BPDE-90 mer and the DNA adducts from A549 cells was also observed.

Using the synthetic BPDE adduct 90-mer as a fluorescent probe and specific monoclonal antibodies to BPDE-DNA adducts, we demonstrated a rapid assay for BPDE-modified DNA in a human lung carcinoma cell line. This approach requires less than 4 min per separation and has excellent resolving power to separate the bound and unbound DNA adducts. The same approach may be extended to assays for other types of DNA damage.

Described in the next series of examples is an assay that combines immunological recognition of damaged DNA, capillary electrophoresis separation, and laser-induced fluorescence detection (Le, et al., 1998; Xing, et al., 2001). A primary (1°) mouse monoclonal antibody specific for the DNA lesion was used to bind to the DNA lesion. A secondary (2°) anti-mouse IgG antibody that was labeled with a fluorescent dye, tetramethylrhodamine (TMR), was used to bind with the primary antibody. The resulting complex of 2° antibody+1° antibody+damaged DNA was separated using free-zone capillary electrophoresis and detected with laser-induced fluorescence. The assay was used to measure thymine glycol, a typical DNA damage induced by ionizing radiation, and to study DNA repair (Le, et al., 1998). Subsequently, the assay was extended to a study of BPDE adducts in DNA from human lung carcinoma cells (A549) that were incubated with nanomolar concentrations of BPDE (Xing, et al., 2001).

Reagents. Unmodified oligonucleotides were synthesized by the Department of Biochemistry DNA synthesis laboratory, University of Alberta, or by Integrated DNA Technologies (Coralville, Iowa). All oligonucleotides were purified by sequencing polyacrylamide gel electrophoresis prior to use. Purity of the oligonucleotides was confirmed by $^{32}$P-radiolabeling and gel electrophoresis. Tetramethylrhodamine (TMR)-labeled oligonucleotide was synthesized by University Core DNA Services, (University of Calgary, AB). (±)-r-7,t-8-dihydroxy-t-9,10-epoxy-7,8,9,10-tetrahydrobenzo[a]pyrene (anti) [(±)-anti-BPDE] was supplied by the National Cancer Institute Chemical Carcinogen Reference Standard Repository (Midwest Research Institute, Kansas City, Mo.). Premixed polyacrylamide/bisacrylamide (19:1) solution was purchased from BioRad Laboratories (Cambridge, Mass.). Enzymes were supplied by Amersham Pharmacia Biotech (Piscataway, N.J.). Monoclonal antibodies 5D11 and 8E11 were purchased from BD PharMingen (San Diego, Calif.). Cell supernatant containing monoclonal antibody E5 (Baan, et al., 1988) was kindly provided by Dr. William Watson, Shell International Chemicals BV, Shell Research and Technology Center, Amsterdam, Netherlands, and was prepared as described by Booth (Booth, et al., 1994). Polyclonal mouse IgG antibody was purchased from Calbiochem (La Jolla, Calif.). Solvents and other biochemicals were supplied by Sigma Chemical (St. Louis, Mo.), Fisher Scientific (Pittsburgh, Pa.), or VWR Canlab (Mississauga, ON, Canada).

Design of probe. In order to imitate DNA damage as it occurs naturally in cellular DNA, we designed a 90-base pair double-stranded oligonucleotide. The desired characteristics of this oligonucleotide were that it be fluorescently-labeled, contain a known amount of damage, and be long enough to be recognized by a variety of antibodies and other DNA-binding proteins. The oligonucleotide consists of six overlapping, complementary oligonucleotides of varying lengths that were annealed and ligated to form a complete double-stranded 90-mer. The oligonucleotide sequences used in the current study were: oligonucleotide 1: 5'-TMR-labeled-CCT-TAAGCTTCCTCAACCACTTACCATACTCGAGATT-3' (SEQ ID NO:2); oligonucleotide 2: 5'-GAGTAT-GG-TAAGTGGTTGAGGAAGCTTAAGG-3' (SEQ ID NO:6); oligonucleotide 5: 5'-GTCATATGCCGCCTCTGA-CCTTC-CTAGAATTCCATCC-3' (SEQ ID NO:8); oligonucleotide 6: 5'-GGATGGAATTCTAGGAAGGTCAG-AGGCGG-3' (SEQ ID NO:9). The sequence of oligonucleotide 3 and its complementary strand (oligonucleotide 4) may be changed to create a variety of desired damage types, typically with a single damaged nucleotide in the middle of oligonucleotide 3. In the current study the sequences used were: oligonucleotide 3: 5'-CCCATTATGCATAACC-3' (SEQ ID NO:5); oligonucleotide 4: 5'-CATATGACGGTTATGCATAATGGG-AATCTC-3' (SEQ ID NO:7). The fluorescent label (oligonucleotide 1) and damaged nucleotide (oligonucleotide 3) are on the same strand to allow both double- and single-stranded DNA studies.

Synthesis of damaged oligonucleotide. (±)-anti-BPDE was used as the model carcinogen for synthesis of the damaged oligonucleotide. A 16-mer with the sequence 5'-CCCATTA TGCATAACC-3' (SEQ ID NO:5) was synthesized to encourage maximum yield of the BPDE-$N^2$ deoxyguanosine (dG) adduct (Margulis, et al., 1993; Funk, et al., 1997). The BPDE-oligonucleotide reaction was based on the procedure described by Margulis (Margulis, et al., 1993), with slight modifications. The 16-mer was diluted in 20 mM phosphate buffer, (pH 11), containing 1.5% triethylamine, to a concentration of 60 mM in a volume of 400 mL. A fresh 3 mM solution of (±)-anti-BPDE in DMSO was prepared, and 40 mL was added to the oligonucleotide solution. This corresponded to a BPDE: oligonucleotide ratio of 5:1. The reaction was carried out at room temperature for 20 hours in the dark with gentle shaking.

Purification of BPDE-oligonucleotide. The components in the BPDE-oligonucleotide reaction mixture were separated using reversed-phase HPLC. The HPLC system consisted of a Dionex (Sunnyvale, Calif.) AGP1 advanced gradient pump with online-degassing module, either an analytical or preparative C18 column, and a Waters (Milford, Mass.) 484 tunable absorbance detector in series with a Shimadzu RF-551 fluorescence HPLC monitor (Columbia, Md.). The detectors were connected to a Hewlett Packard Model 35900 multichannel interface (Palo Alto, Calif.), which converted the signals for use by a computer running ChemStation software (Hewlett Packard, Palo Alto, Calif.). Preparative separation was carried out on a 10.0×250 mm, 5 mm Luna C18(2) preparative column (Phenomenex, Torrance, Calif.). The reaction products were initially assessed on the analytical column using a protocol described previously (Margulis, et al., 1993; Cosman, et al., 1990). This procedure employed a linear 0-90% methanol gradient in 20 mM sodium phosphate buffer (pH 7.0) in 60 min, with a flow rate of 0.75 mL/min. To reduce separation times for large volumes of the reaction mixture, HPLC purification of the BPDE-16-mer was carried out in two steps. The first separation was under isocratic conditions, using a mobile phase of 70% methanol/30% 20 mM sodium phosphate, pH 7.0 buffer and a flow rate of 0.75 mL/min and 3.5 mL/min for the analytical and preparative columns, respectively. Elution of products were monitored in series by the absorbance detector (wavelength=260 nm for DNA) and the fluorescence detector (excitation wavelength=343 nm, emission wavelength=400 nm for BPDE). This first separation removed unreacted BPDE as well as the tetrol hydrolysis products. DNA fractions were collected, dried using a centrifugal evaporator, and redissolved in distilled deionized water (dd$H_2$O). The second separation consisted of a linear 10-40% methanol/20 mM sodium phosphate, pH 7.0 buffer gradient in 7.5 min (4%/min) followed by an additional 5 minutes at 40% methanol. This separated the BPDE-oligonucleotide from unreacted oligonucleotide. BPDE-oligonucleotide fractions were collected, dried to remove methanol and redissolved in dd$H_2$O. The samples were desalted using Sep-Pak C18 reversed-phase columns (Waters). The sample was applied to a prepared Sep-Pak cartridge, then washed with 10 mL of the following solutions: 25 mM ammonium bicarbonate (pH 8.0); 25 mM ammonium bicarbonate/5% acetonitrile; $H_2$O/5% acetonitrile; $H_2$O/5% acetonitrile. The BPDE-oligonucleotide was then eluted with 4×1 mL of $H_2$O/30% acetonitrile, dried and redissolved in dd$H_2$O.

Synthesis and purification of 90-mer oligonucleotides. Prior to ligation with the other 5 oligonucleotides, it was necessary to phosphorylate the freshly purified BPDE-16-mer at the 5'-end. Reaction mixtures included: ~200 pmol of BPDE-16-mer or control 16-mer, 4 mL of 100 mM ATP (400 pmol), 1.2 mL of 10× polynucleotide kinase reaction buffer, and dd$H_2$O to a total volume of 12 mL. T4 polynucleotide kinase (PNK) was added (1 mL, 6.1 units/mL), then samples were mixed and incubated at 37° C. for 1 hour. After complete reaction, the excess PNK was heat denatured at 70° C. for 10 minutes. The 16-mers were then mixed with the TMR-labeled 37-mer and the other 4 oligonucleotides so that all would be in 2:1 excess over the 16-mers. 5× DNA ligase buffer was added to a final concentration of 1× and the mixture was heated in a water bath to 70° C. for 10 minutes, then allowed to cool over several hours to room temperature. DNA ligase was added (2 mL, 8.5 Weiss units/mL) and the sample incubated overnight at 16° C.

Purification of the BPDE and control ligation products was achieved using preparative, 7.5% native polyacrylamide gel electrophoresis (PAGE). Electrophoresis was carried out at 600 V for 6 hours with a water cooling core to prevent denaturation of the ligation products. The bands were visualized by brief exposure to ultraviolet light, causing the TMR label to fluoresce, and cut from the gel. The gel slices were crushed and soaked to elute the products overnight in 0.3 M sodium acetate, pH 5.2 on a rotary shaker protected from light. After elution, polyacrylamide fragments were removed from solution using filter units prepared in the lab. The solution was passed through silanized glass wool followed by GF/C glass microfibre filter paper (Whatman). The samples were then extracted and back-extracted with equal volumes of phenol/chloroform/isoamyl alcohol (25:24:1) followed by chloroform/isoamyl alcohol (24:1). Oligonucleotides were precipitated by adding Mg$Cl_2$ to 10 mM and 3 volumes of ice-cold 95% ethanol and, then placed at −20° C. overnight. The following day samples were centrifuged for 45 minutes at 14000 rpm and 4° C., supernatant was removed, and the pellets were washed once with 95% ethanol. Samples were again centrifuged for 10 minutes, dried and redissolved in dd$H_2$O. UV-Vis absorbance scans were performed on the resulting oligonucleotide solutions to determine concentration as well as to confirm the presence of the TMR dye and BPDE moiety.

Instrumentation for analysis of ligation products. was the same as described in examples 11-13. with the following modification. The system was equipped with an auxiliary microscope to assist in the alignment of the optics. The microscope was used to visualize the position of the laser beam with respect to both the sample flow through the capillary and the collection optics, represented by a light-emitting diode (LED) positioned behind the pinhole in the collection assembly. Alignment was achieved by initially fixing the position of the collection assembly, then adjusting the capillary and laser-focusing objective using X-Y-Z translation stages. The angle of the fluorescence-collecting objective and the position of the collection assembly were also adjustable for optimization of alignment.

Samples were electrokinetically injected into the capillary by applying an injection voltage of 10000 V for 5 seconds. The separation was carried out at room temperature with a separation voltage of 20000 V. The running buffer used was 1× Tris-glycine (25 mM Tris, 250 mM glycine), pH 8.3. The capillary was washed approximately every 5-10 injections with 0.1 M NaOH (applied by syringe for 1 min) followed by electrophoresis using 1× Tris-glycine, pH 8.3 for 7 minutes. The initial voltage was kept low to prevent excessive joule heating in the capillary. As the running buffer replaced the NaOH in the capillary, current decreased allowing the running voltage to be gradually increased to 20000 V for the final 5 minutes of the reconditioning period. All capillary electrophoresis data were analyzed using Igor Pro software (version 3.1, WaveMetrics Inc., Lake Oswego, Oreg.).

Characterization of BPDE and control 90-mers. Prior to analysis, 90-mer samples were diluted to appropriate concentrations in running buffer (1× Tris-glycine, pH 8.3). The 90-mer products were analyzed either in their native form or their denatured, single-stranded form. Denaturation of the 90-mers was achieved by heating the samples at 100° C. for 10 minutes in a heating block, then transferring directly to ice to prevent reannealing. After cooling, the samples were briefly centrifuged in a microcentrifuge to collect condensation from the side of the tube, then gently mixed to ensure a homogenous solution. Total sample volume was typically 20 mL, which allowed for convenient injection into the capillary. For experiments involving antibodies, fresh dilutions of antibody stock solutions were prepared immediately before analysis and kept on ice. After addition of antibody to the 90-mer solution, the sample was gently vortexed to ensure complete mixing.

Treatment of A549 cells with BPDE. A human lung carcinoma cell line (A549) was incubated with BPDE to produce DNA adducts in genomic DNA. The cell line was maintained in DMEM/F12 medium (Gibco BRL, Gaithersburg, Md.) supplemented with 10% fetal bovine serum. The cells were seeded at $1\times10^5$ cells per plate and maintained at 95% humidity and 5% $CO_2$ for 20 hours prior to the addition of BPDE. Old culture media were removed from each culture plate and the cells were washed twice with phosphate buffered saline (PBS). Media containing BPDE at various concentrations (0, 2.5, 5, and 10 mM final concentration) were added to the designated plates. The cells were further incubated in the media containing BPDE for 2 hours. The cells were then washed with PBS prior to the addition of DNAzol lysis reagent (Gibco BRL) to facilitate cell lysis and DNA extraction. Subsequent steps involved a 99.9% ice cold ethanol precipitation and a 70% cold ethanol wash to purify the genomic DNA. The final DNA pellet was dissolved in distilled deionized water (dd$H_2O$) and DNA concentration was measured at $OD_{260}$ using dd$H_2O$ as a blank.

Competitive assay for BPDE-DNA adducts. The DNA samples from the A549 cells were analyzed for BPDE-DNA adducts by competitive assay using the TMR-labeled 16-mer or 90-mer oligonucleotides as probes. Mixtures containing 60 nM of the oligonucleotide probe, 0.4 mg/mL of mouse monoclonal antibody 8E11, and 80 mg/mL of the DNA from A549 cells were incubated in 20 mL of tris-glycine buffer (25 mM tris and 200 mM glycine, pH 8.3) at room temperature for 30 min. These were subjected to CE/LIF analysis to detect both antibody-bound and unbound fluorescent probes.

Example 14

Using CE/LIF to determine Affinity interactions of BPDE-90-mers with a monoclonal antibody. The purification of BPDE-16-mer oligonucleotide, the synthesis and purification of BPDE 90-mer ligation products, and the characterization of the BPDE 90-mer ligation products were carried out as known to those skilled in the art.

Preliminary experiments using monoclonal antibody 8E11 demonstrated that the specific antibody bound to the BPDE-90 mer, not the control 90 mer. These results were obtained by first denaturing the 90-mers ($5\times10^{-9}$ M), then adding 8E11 antibody to a final concentration of 20 mg/mL and incubating for 10 min at room temperature (21° C.). The same fluorescence intensity scale was used for both 90-mers for ease of comparison. For the mixture of the BPDE 90-mer and 8E 11, an additional peak was present in the electropherogram with a migration time of approximately 3.0 min. This peak represented the complex between the antibody and single-stranded BPDE-DNA, and was well-resolved from the denatured 90-mer peak at 4.1 min. When comparing the fluorescent signals between runs, the total area of the two peaks for the mixture of BPDE 90-mer and 8E11 was very similar to the area of the peak for the BPDE 90-mer alone. The formation of an antibody-DNA complex was not observed with the control 90-mer, indicating a specific interaction of the antibody with the BPDE 90-mer.

The effect of incubation time and temperature on complex formation were investigated using the same concentrations of BPDE 90-mer ($5\times10^{-9}$ M) and 8E11 (20 mg/mL). For incubations carried out at both room temperature and on ice, the interaction did not change significantly between 1 min and 20 min. At room temperature, the complex was stable after 45 min. For incubation on ice, the complex decreased slightly after 45 min when compared to the 20 min incubation. In general, room temperature incubations with 8E11 resulted in more stable and reproducible complex formation than incubations on ice. This result is expected since the recommended temperature for conventional immunoassays using 8E11 is 37° C. (Santella, et al., 1984; Hsu, et al., 1995), and most immunochemical procedures require incubation temperatures of either 37° C. or room temperature. Based on these results, further experiments with 8E11 antibody were carried out at room temperature. An incubation time of 5 min was chosen for ease of sample preparation and analysis.

Overnight incubations resulted in a decrease of the DNA-antibody complex, as well as a reversion to the doublet shape for the free 90-mer peak. This result suggests that 90-mer samples left overnight tended to re-anneal to the double-stranded form, causing dissociation of the DNA-antibody complex. This also implies that the affinity of 8E11 for double-stranded BPDE-DNA is less than for single-stranded BPDE-DNA.

The difference in affinity of 8E11 antibody between single- and double-stranded BPDE-modified DNA was further confirmed by comparing its binding with heat-denatured BPDE 90-mer and native BPDE-90 mer (20 mg/mL 8E11). Antibody-oligonucleotide complex formation was approximately 6 fold higher for the denatured single-stranded 90-mer than the native form. Thus, denaturation of samples by heat before incubation with antibodies was retained for further experiments.

Example 15

Using CE/LIF to Determination of specific antibody using BPDE-90 mer as a probe. An application of the fluorescent BPDE-90 mer probe was demonstrated for the determination of anti-BPDE antibody. Calibration from the analyses of mixtures containing different amounts of 8E11 and a constant concentration of the detatured BPDE-90 mer probe ($5\times10^{-9}$ M) were made. A DNA-antibody complex peak was observed with 8E11 concentrations as low as 0.1 mg/mL. This concentration corresponds to $0.7\times10^{-9}$ M (or 0.7 nM) assuming a molecular weight of approximately 150,000 for the antibody 8E11. The concentration of BPDE-90 mer (5 nM) was in excess and the formation of its complex with the antibody was not complete. The amount of the complex increased at higher concentrations of 8E11, up to 10 mg/ml (7 nM). At this concentration complex formation appeared to reach saturation, since further increase of antibody concentrations did not increase the proportion of 90-mer bound to 8E11.

Example 16

Using CE/LIF for Screening for anti-BPDE antibodies using the fluorescent BPDE-90mer probe. The fluorescent BPDE-90 mer probe was further used to screen for specific binding proteins, with 3 antibodies as model protein analytes. Monoclonal antibodies 8E11, 5D 11 and E5 are all specific for BPDE-modified DNA. A comparison between these antibodies was conducted to determine differences in their reactivity to the BPDE 90-mer standard as well as their behavior in the capillary electrophoresis system. Conditions used for sample preparation were identical to earlier experiments: heat denaturation of the 90-mer at 100° C. for 10 min, cooling on ice, then incubation with antibody at room temperature for 5 min before injection. Polyclonal mouse IgG was used as a negative control since it is essentially the same molecular structure (isotype) as the monoclonal antibodies but is not expected to react with the BPDE 90-mer. The BPDE 90-mer probe concentration was fixed at $5\times10^{-9}$ M and the antibodies were added in varying amounts. All three monoclonal antibodies reacted with the 90-mer probe, with 8E11 giving the highest formation of complex. The negative control showed a very slight reactivity but was insignificant compared to the other antibodies, even at concentrations up to 40 mg/mL.

Antibodies 8E11 and E5 were found to bind specifically to the BPDE adduct. No cross-reactivity with the unmodified control 90-mer was observed for either 8E11 or E5. The antibody 5D11 showed slight cross-reaction with undamaged DNA. When incubated with 20 μg/mL 5D 11, the control 90-mer formed a peak corresponding to antibody complex, with about 2.1% of total peak areas as compared with the BPDE 90-mer. This non-specific interaction between 5D11 and undamaged DNA is in agreement with previous studies (Santella, et al., 1984) that have demonstrated cross-reactivity, and is a result of its being raised against a full-length BPDE-DNA antigen. Both 8E11 and E5 were raised against BPDE-guanosine monomers conjugated to carrier proteins (Baan, et al., 1988; Santella, et al., 1984) and therefore do not recognize undamaged DNA.

The incomplete binding of the DNA damage probe with the antibodies (up to 50% of binding) is probably because the probe is a mixture of several BPDE-90 mer isomers. The stereochemistry of the BPDE-$N^2$-dG adduct could be important to its binding with specific antibodies. In the preparation of the BPDE-modified 16-mer, (±)-anti-BPDE was reacted with the oligonucleotide. The covalent bond that forms between BPDE and guanosine may be either cis- or trans-relative to the hydroxyl group on the adjacent carbon atom. Therefore, there may be as many as four different configurations of the BPDE 16-mer: (+)-trans, (+)-cis, (−)-trans, and (−)-cis (2). The reaction protocol was designed to minimize the formation of cis- adducts (Funk, et al., 1997), but a mixture of (+)-trans and (−)-trans adducts with a small amount of cis adducts would be expected in the BPDE 16-mer reaction products (Cosman, et al., 1990). Because these stereoisomers were pooled together after purification by HPLC and before the ligation reaction, the 90-mer product would also contain these configurations. The advantage of this mixture is that it more accurately represents the spectrum of damage that would occur in human DNA samples. The disadvantage is that BPDE-DNA antibodies exhibit different affinities for these stereoisomers (Hsu, et al., 1995). In competitive inhibition studies using BPDE-modified 11-mers, Hsu (Hsu, et al., 1995) demonstrated a lower affinity for the (−)-trans-anti-BPDE-$N^2$-dG adduct than for the (+)-trans-anti-BPDE-$N^2$-dG adduct. For antibodies 8E11 and 5D11 this lower affinity was 66% and 20% of the (+)-trans adduct, respectively. Both antibodies exhibited much lower affinities for the cis adducts compared to the (−)-trans adduct. Since the 90-mer contained a combination of both trans adducts, the stereospecific difference in affinity may in part be responsible for the differences in complex formation observed for these antibodies. The presence of different BPDE-90mer isomers may also contribute to the observed incomplete binding. The other possible reason for the incomplete binding is the presence of residual oligonucleotides that do not contain BPDE and therefore, do not bind to the antibodies.

In addition to the isomer-specific reactivities, Hsu (Hsu, et al., 1995) showed a difference in affinity between 8E 11 and 5D 11 when considering only the (+)-trans adduct. 8E 11 was approximately 7 times more sensitive than 5D11 for the very short 11-mer oligonucleotide. For full-length heat-denatured BPDE-DNA, the two antibodies were almost identical. This difference is likely due to the antigens against which these antibodies were raised: BPDE-$N^2$-dG mononucleotide for 8E11, full-length BPDE-DNA for 5D 11. 5D11 may require a longer sequence of DNA surrounding the damaged site for binding which would not be present in the 11-mer. Given these results one might predict that for DNA of intermediate length (90 bases), 8E11 would still have a higher affinity than 5D11, but to a lesser extent. These results are consistent with previous findings, which indicates that monoclonal antibody 8E11 is likely the best choice for detecting BPDE-damaged DNA using the capillary electrophoresis/laser-induced fluorescence assay.

Example 17

Using CE/LIF and the BPDE-DNA probe in a competitive assay for BPDE-DNA adducts in cells. The 90-mer probe described herein has many potential uses in DNA damage research. It enables the investigation of alternative assay methods, including CE-based competitive immunoassays (Tao, et al., 1996; Ye, et al., 1998; Lam, et al., 1999; Wan, et al., 1999) using the probe as a fluorescent probe (competitor). This approach is based on competition between damaged DNA and the fluorescent probe for the binding sites of a limited amount of antibody. With little or no damaged DNA in a sample, the probe achieves maximum complex formation with the antibody. As the amount of damaged DNA in the sample mixture increases, the probe is displaced from the antibody. This would result in an increase in the free probe peak and a decrease in the probe-antibody complex peak. This method has been demonstrated by using oligonucleotide and genomic DNA containing BPDE-damaged sites (Tan, et al., 2001). Electropherograms from the analysis of BPDE-DNA adducts in A549 cells that were incubated with 2.5, 5, and 10 mM BPDE for 2 hr were collected. Again, increasing amounts of BPDE-DNA adducts were formed as the cells were incubated with increasing concentrations of BPDE. The BPDE-DNA adducts compete with the TMR labeled BPDE-DNA adduct probe for the antibody binding, resulting in the corresponding increase of the unbound probe (peak 3) and decrease of antibody complexes (peaks 1 and 2) of the fluorescent probe. This analysis requires less than 4 min per separation and has excellent resolving power to separate the bound and unbound DNA adducts. The same approach may be extended to assays for other types of DNA damage.

Another important aspect of the probe's design is the flexibility to substitute different damage types in the molecule with relative ease. The sequences of the two center oligonucleotides may be changed depending on the desired modification. By inserting these different damaged oligos, a variety of DNA damage detection systems can be investigated using the corresponding damage probe and CE/LIF. The technique itself combines specific recognition with high sensitivity detection, minimal sample preparation, and fast analysis times (5 minutes per run).

Example 18

Using CE/LIF to Determine Stoichiometry of antibody binding with TMR-BPDE-16-mer (16mer*) oligonucleotide. In this example CE/LIF is used to determine the binding stoichiometry of DNA adducts with antibodies. Advantage is taken of the fact that both size and charge of the molecules contribute to CE separation. If additional charges can be introduced to the complex due to binding, then the separation of the multiple complexes becomes possible. Fluorescent oligonucleotide probes that contain a single adduct which can be recognized by an antibody were designed. These probes introduce large mobility changes to the antibody when bound to the probe because of the highly negative charge of the probe. With these probes, we are able to study the binding stoichiometry between oligonucleotides and the antibody. DNA adducts of benzo[a]pyrene diol epoxide (BPDE) were looked at in this example. Available monoclonal IgG antibody has a high affinity for BPDE-DNA adducts, allowing detailed information on binding stoichiometry between the antibody and the DNA adducts to be obtained. This example provides direct information on antibody binding stoichiometry.

Reagents: Oligonuleotides were synthesized by the Department of Biochemistry DNA synthesis laboratory, University of Alberta, or by Integrated DNA Technologies (Coralville, Iowa). All oligonucleotides were purified by sequencing polyacrylamide gel electrophoresis prior to use. Purity of the modified oligonucleotieds was confirmed by gel electrophoresis and $^{32}$P-postlabeling. Tetramethylrhodamine (TMR)-labeled oligonucleotide was synthesized by University Core DNA Services, (University of Calgary, AB). (±)-r-7,t-8-dihydroxy-t-9,10-epoxy-7,8,9,10-tetrahydrobenzo[a]pyrene [(±)-anti-BPDE] was supplied by the National Cancer Institute Chemical Carcinogen Reference Standard Repository (Midwest Research Institute, Kansas City, Mo.). Mouse monoclonal antibody 8E11 was purchased from BD PharMingen (San Diego, Calif.). Polyclonal rabbit IgG antibody was purchased from Calbiochem (La Jolla, Calif.). Solvents and other biochemicals were supplied by Sigma (St. Louis, Mo.), Fisher Scientific (Pittsburgh, Pa.), or VWR Canlab (Mississauga, Ontario).

Synthesis of BPDE-DNA adducts: Two 16-mers with the sequence 5'-CCCATTATGCATAACC-3' (SEQ ID NO:5) were synthesized and reacted with BPDE to yield the BPDE-$N^2$ deoxyguanosine (dG) adduct (Margulis, et al., 1993; Funk, et al., 1997). One of the 16-mer oligonucleotides was labeled with TMR at the 5' end, and the other was not labeled. The formation of BPDE-oligonucleotide was based on the procedure described by Margulis (Margulis, et al., 1993) with slight modifications. The 16-mer was diluted in 20 mM phosphate buffer (pH 11) containing 1.5% triethylamine, to a concentration of 60 mM in a volume of 400 mL. To the oligonucleotide solution was added 40 mL 3 mM BPDE in DMSO. This corresponded to a BPDE:oligonucleotide ratio of 5:1. The reaction was carried out at room temperature for 20 hours, in the dark with gentle shaking. The double stranded TMR-BPDE-90-mer and BPDE-90-mer were constructed through ligation of BPDE-16-mer with five other oligonucleotides.

Purification of TMR-BPDE-oligonucleotide: The components in the TMR-BPDE-oligonucleotide reaction mixture were separated using reversed-phase HPLC. The HPLC system consisted of a Dionex (Sunnyvale, Calif.) AGP1 advanced gradient pump with online degassing module, an analytical C18 column, a Waters (Milford, Mass.) 484 tunable absorbance detector in series with a Shimadzu (Tokyo, Japan) RF-551 fluorescence detector. The detectors were connected to a Hewlett Packard (Palo Alto, Calif.) Model 35900 multichannel interface, which converted the signals for use by a computer running ChemStation software (Hewlett Packard). The analyses were performed using a Luna C18(2) analytical column (4.6×250 mm, 5 mm, Phenomenex, Torrance, Calif.). The reaction products were purified initially using a gradient elution. This procedure employed 10 mM sodium phosphate buffer (pH 7.0) and acetonitrile. The acetonitrile content was initially 10%, linearly ramped to 15% during the first 20 min, and then kept at 15% for 5 min. After the BPDE-modified oligonucleotides were eluted and collected, the column was washed using 50% acetonitrile for 20 min to remove unreacted BPDE and its metabolites. The flow rate was 1.0 mL/min. Elution of products were monitored in series by an absorbance detector (wavelength=260 nm for DNA) and a fluorescence detector (excitation wavelength=535 nm, emission wavelength=580 nm for TMR). The fractions containing the BPDE-oligonucleotide were pooled and further purified to remove any unmodified oligonucleotides. This second HPLC purification step was carried out using an isocratic elution with 10 mM phosphate buffer (pH 7.0), containing 12.5% acetonitrile as mobile phase. Other HPLC conditions were the same as described above. The collected fractions were concentrated by pressurized air under room temperature and dissolved in distilled deionized water (ddH$_2$O). The purified BPDE-oligonucleotides were evaluated using HPLC under isocratic elution conditions, and showed good purity of above 95%. The concentration of the final TMR-BPDE-16-mer was estimated using absorbance at 260 nm.

Instrumentation for analysis of the DNA-BPDE adducts: Analysis and characterization of the DNA-BPDE adducts was carried out using a laboratory-built capillary electrophoresis laser induced fluorescence (CE/LIF) system as described in examples 13 on.

Samples were electrokinetically injected into the capillary by applying an injection voltage of 15 kV for 5-10 seconds. The separation was carried out at room temperature with a separation voltage of 15 kV. The running buffer were either 1× tris-glycine (25 mM Tris, 192 mM glycine, pH 8.3) or 0.5× tris-glycine (12.5 mM tris and 96 mM glycine, pH 8.3). The capillary was washed approximately every 3 injections with 0.02 M NaOH electrophoretically at 15 kV for 7 min followed by electrophoresis using water and the running buffer for 7 min each. All capillary electrophoresis data were analyzed using Igor Pro software (version 3.1, WaveMetrics Inc., Lake Oswego, Oreg.).

Complex formation of TMR-labeled BPDE-DNA adducts and antibody: TMR-BPDE-16-mer and TMR-BPDE-90-mer samples were diluted to appropriate concentrations in running buffer (tris-glycine, pH 8.3). The double stranded BPDE-90-mer was denatured by heating at 95° C. for 5 min in a heating block. It was then placed on ice to prevent reannealing. After cooling, the samples were briefly centrifuged in a microcentrifuge (Z233M, Hermle) to collect condensation from the side of the tube, then gently mixed to ensure a homogenous solution. TMR-BPDE-16-mer was synthesized as a single-stranded oligonucleotide. Appropriate dilutions of antibody stock solutions were prepared immediately before use and kept on ice. After addition of antibody to the BPDE-oligonucleotide solutions, the samples were gently vortexed to ensure complete mixing and incubated at the room temperature for 5-10 min, then analyzed by CE/LIF. The total sample volume was typically 20 mL.

Simultaneous binding of two BPDE-DNA adducts to the antibody: Both TMR-labeled and unlabeled BPDE-adducts were allowed to bind with the antibody. The freshly diluted BPDE-16-mer (16mer) and TMR-BPDE-16-mer (16mer*) solutions were mixed together before addition of the antibody. Concentrations of the TMR-BPDE-16-mer and the antibody were kept constant at 9.6 nM and 33.3 nM, respectively, and the unlabeled BPDE-16-mer was varied from 2.5 nM to 5.0 mM. The sample mixtures were incubated for 5 min at room temperature, then analyzed by CE/LIF. Similarly, the antibody was added to mixtures of the TMR-BPDE-16mer and BPDE-90mer to study the competitive binding and ligand exchange.

A series of electropherograms from CE/LIF analyses of mixtures containing 24 nM TMR-BPDE-16-mer (16mer*) and varying concentrations of mouse monoclonal antibody (Ab) to BPDE, from 0.5 mg/mL to 16.0 mg/mL were collected. In these mixtures, 2 complexes between the Ab and the TMR-labeled BPDE-16-mer (16mer*) can be expected as follows:

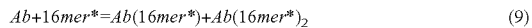

$$Ab + 16mer^* = Ab(16mer^*) + Ab(16mer^*)_2 \quad (9)$$

The free (unbound) 16mer* gives a peak that was well resolved from the two complexes. The unbound 16mer* oligonucleotide and the antibody-bound 16mer* complexes are negatively charged. Under the free zone CE separation conditions, the direction of their electrophoretic mobility ($\mu_{ep}$) is opposite to that of the electroosmotic flow (EOF). Among the three fluorescent species the unbound 16mer* has the highest negative effective charge. It has the highest electrophoretic mobility towards the positive (injection) end, and thus the longest migration time (3.4 min); When the 16mer* binds to an antibody molecule, the reduction of the effective charge results in a smaller electrophoretic mobility and thus a shorter migration time (2.1 min). When the Ab binds to two 16mer* molecules, the charge density of the complex is between those of the Ab(16mer*) complex and the unbound 16mer*. Therefore, a smaller mobility shift is expected. Indeed, we observed the Ab(16mer*)$_2$ complex at 2.4 min. The two complexes are well resolved from each other, (resolution of 1.55).

It is evident that formation of the two complexes depends on the relative concentrations of the TMR-BPDE-16-mer oligonucleotide (16mer*) and the antibody. The intensity of Ab(16mer*) complex (1:1 stoichiometry, peak 1) increases with increasing concentration of the antibody, whereas the Ab(16mer*)$_2$ complex (1:2 stoichiometry, peak 2) reaches a maximum at an antibody concentration of 1.0 μg/mL and then decreases gradually with increasing concentrations of the antibody.

The primary complex of the 1:1 stoichiometry increases with increasing concentration of antibody. When the concentration of the antibody is 8-16 μg/mL, approximately 80-85% of the total 16mer* oligonucleotide is present as the primary complex with the antibody (1:1 stoichiometry). Formation of the secondary complex, Ab(16mer*)$_2$ (1:2 stoichiometry) is favored at lower concentrations of the antibody, when the 16mer* oligonucleotide is in excess. The amount of the secondary complex reaches a maximum at the antibody concentration of 1 μg/mL, when 50% of the total 16mer* is present as the secondary complex. As the molecular weight of the mouse monoclonal antibody IgG is approximately 150,000 Da, an antibody concentration of 1 μg/mL is approximately 7 nM. Although the Ab(16mer*)$_2$ complex is observed throughout the entire antibody concentration range studied, from 0.02 μg/mL (~0.14 nM) to 16 μg/mL (~100 nM), it is predominant only when the antibody concentration is below 2 μg/mL (~14 nM) and is lower than the concentration of the 16mer* (24 nM). At similar concentrations of antibody (4 μg/mL or 27 nM) and the 16mer* (24 nM), the primary complex dominants, suggesting that the complex with one binding site is preferred.

To further study the secondary complex, varying concentrations of the 16mer* (2.4-19.2 nM) were mixed with a fixed concentration of the antibody (0.4 μg/mL or ~2.7 nM), and the mixtures were analyzed using CE/LIF. Fluorescence intensity of the secondary and primary complexes as a function of the concentration of the fluorescently labeled BPDE-16-mer (16mer*) were measured. At a lower concentration of the 16mer* (2.4 nM) than the antibody concentration (2.7 nM), the peak intensity of the primary complex is comparable to that of the secondary complex. When the 16mer* concentration is higher (4.8-19.2 nM) than the antibody concentration (~2.7 nM), the secondary complex dominates. The fluorescence intensity of the secondary complex increases with increasing amounts of the 16mer* until it reaches a plateau at approximately 17 nM when the amount of the antibody presumably becomes the limiting factor.

Most previous studies on immunoassays were not able to address the binding stoichiometry although multiple complexes might have formed. The present study clearly shows the formation of primary and secondary complexes. The behavior may be qualitatively explained by a two binding site model. The mouse monoclonal antibody is an IgG, which has two specific binding sites for antigen (hapten), in this case, BPDE-16-mer oligonucleotide. When an antibody is in excess of antigen, there are more available binding sites for antigen, thus most complex exists as the primary complex (1:1 stoichiometry).

Only when the binding sites are limited as in the case of lower antibody concentration, the secondary complex (1:2 stoichiometry) dominates. These results suggest that binding to the second sites of antibody is less favored probably because of possible steric hindrance by the binding on the first site.

Example 19

Using CE/LIF to Determine the Binding of the antibody with TMR-BPDE-90-mer (90mer*): To confirm the preferential binding to the first site and the possible hindrance to the secondary binding, we further compared binding of the antibody with a TMR-BPDE-90-mer (90mer*) oligonucleotide. The 90mer* is approximately 28,000 Da, about five times higher than the 16mer* (µ5,000 Da). Eelectropherograms from CE/LIF analyses of samples containing 50 nM 90mer* incubated with varying concentrations of mouse monoclonal antibody, 0-20 µg/mL (0-140 nM) were collected. In the absence of antibody, the 90mer* gave a single peak at migration time of 3.2 min. After incubation with the antibody, two additional peaks are present in the electropherogram with migration times of 2.41 and 2.60 min. These peaks represent the complexes between the antibody and single stranded 90mer* oligonucleotide. Because of the electrophoretic mobility shift, they are well resolved from the unbound 90mer*. Despite the small difference in migration time between the two complexes (0.19 min), these two complexes are baseline resolved. The first peak is due to the primary complex of the antibody and DNA adduct with 1:1 stoichiometry, and peak 2 is due to the secondary complex of 1:2 stoichiometry.

The binding of the anti-BPDE antibody with TMR-BPDE-90-mer appears to be weaker than the binding with TMR-BPDE-16-mer. Approximately 60% of the total 90mer* (50 nM) formed complex with the antibody when the concentration of antibody was ~140 nM. This percentage is lower than that for the 16mer* where 80-85% of the total 16mer* (24 nM) complexed with the antibody (50-100 nM). This is not surprising considering that the antibody (mouse monoclonal, 8E11) was raised against BPDE-adduct of mononucleotide and perhaps has a higher affinity to shorter stretches of DNA.

The ratio of the primary and secondary complexes was also found to depend on the relative concentrations of the antibody and the 90mer*, similar to that shown in the 16mer* experiments described above. However, the secondary complex of the antibody with the 90mer* is less stable than the secondary complex of the same antibody with the 16mer*. The primary complexes of the antibody with both the 90mer* and the 16mer* are much more stable. The results support our suggestion that the primary binding is stronger than the secondary binding. Despite the identical sequence and structure of the two binding sites of the monoclonal IgG antibody, it is likely that the secondary binding is affected by the primary binding on the first site. This may be caused by a conformational change of the antibody structure after binding to one site. Alternatively, steric hindrance of the molecule bound to one site of the antibody may affect the binding of another molecule on the second site of the same antibody molecule. A comparison of our results on the 16mer* and 90mer* indicates that the secondary binding with the larger 90mer* is less favored. These results suggest that steric hindrance plays an important role in the formation of the secondary complex between an antibody and an antigen.

Example 20

Using CE/LIF to measure competitive binding of antibody with TMR-BPDE-16-mer and unlabeled BPDE-16-mer: The commonly used competitive immunoassays are based on competitive binding of two ligands to a limiting amount of antibody. Typically, one ligand is labeled and is used as a detection probe. The target analyte is usually the unlabeled ligand. In the traditional competitive assay format, the analyte (unlabeled ligand) can only be indirectly determined through monitoring the relative intensity of signals produced from the labeled ligand. In this study, It was found that the primary and secondary complexes of the antibody with the ligands can be separated. Thus, we decided to further study the binding of multiple ligands to the antibody, with a possibility of developing new approaches to binding assays.

Electropherograms from CE/LIF analyses of mixtures containing 33 nM antibody, 35 nM TMR-BPDE-16-mer (16mer*), and varying concentrations (0, 0.05, 0.5 and 5.0 mM) of unlabeled. BPDE-16-mer (16mer) were collected. In the absence of the unlabeled BPDE-16-mer, the primary complex [Ab(16mer*)] dominates and its fluorescence intensity is much higher than that of the secondary complex [Ab(16mer*)$_2$].

While the primary complex decreases with increasing concentrations of the competing unlabeled 16mer, a typical competitive immunoassay behavior, the secondary complex increases initially with increasing concentrations of the 16mer. The latter behavior is unique and has not been reported previously with competitive immunoassays. This observation can be explained as following.

The present CE/LIF technique allows the separation of two antibody complexes when a labeled ligand (L*) (e.g., 16mer*) is mixed with the antibody.

$$Ab+L^*=AbL^*+AbL^*_2 \quad (10)$$

To allow for detection of an unlabeled ligand (L), competitive immunoassay approaches rely on the competition of unlabeled ligand (L) with the labeled ligand (L*) for the limiting amount of antibody (Ab). Following species may be formed:

$$AbL^*+L=AbL+L^* \quad (11)$$

$$AbL^*+L=AbL^*L \quad (12)$$

$$AbL^*_2+L=AbL^*L+L^* \quad (13)$$

$$AbL^*_2+2L=AbL_2+2L^* \quad (14)$$

The species that are fluorescent and can be detected include the free ligand L*, the primary complex AbL*, and the secondary complexes AbL*L and AbL$_2$*. It is clear that the end products are a redistribution of L* and L in the complexes although L* and L compete for the same antibody.

The relative changes of the primary and secondary complexes with varying concentrations of unlabeled 16mer when it is incubated with 9.6 nM TMR-labeled 16mer* and 33 nM (5 µg/mL) antibody were measured. When the concentration of the unlabeled 16mer is below 10 nM, the primary complex [Ab(16mer*)] dominates and its amount remains almost constant with increasing concentration of the unlabeled 16 mer up to 10 nM. The total ligand concentration (16mer* and 16mer) is lower compared with that of the antibody, and there are excess antibody binding sites available. Thus, no significant competition between the two ligands takes place. Increasing the competing 16mer concentration from 10 nM to 200 nM result in the reduction of the primary complex in a manner similar to that commonly observed for conventional competitive assay. Further increase of the unlabeled 16mer concentration to above 250 nM results in disappearance of the primary Ab(16mer*) complex, probably due to the displacement of the 16mer* by the excess 16mer:

$$Ab(16mer^*)+16mer=Ab(16mer)+16mer^* \quad (15)$$

The secondary complexes initially increases with increasing concentration of the unlabeled 16mer, and reaches a maximum when the concentration of the 16mer is 100 nM. This behavior is different from that of traditional competitive immunoassays where only the mixture of antibody complexes are commonly detected and the separation of the 1:1 and 1:2 complexes is not available for examination. Further increase of the 16mer concentration (100-1000 nM) results in a gradual decrease of the secondary complex. Only at this high concentration range (100-10000 nM) of the competing 16mer was the competitive immunoassay behavior observed.

When the secondary complex and the unlabeled BPDE-16-mer are plotted using logarithm scales, two linear lines are observed. A linear correlation coefficient of 0.97 and a positive slope are observed between the secondary complex and the concentration of the 16mer below 100 nM. This region probably corresponds to redistribution of the ligands. Above 100 nM, a linear correlation of 0.997 and a negative slope are observed. This may indicate competition with limited amount of antibody. These two linear lines clearly distinguish the competition and redistribution, and can be used as quantitative curves for different concentration zones.

It is expected that two types of the secondary complexes could be formed: one antibody bound to two TMR-BPDE-16-mer [Ab(16mer*)$_2$] and one antibody bound to one TMR-BPDE-16-mer and one BPDE-16-mer [Ab(16mer*)(16mer)]. These two secondary complexes of 16-mer cannot be separated since there is only slight difference between the TMR-labeled and unlabeled 16-mer oligonucleotides. However, the two secondary complexes can be observed using a different competing oligonucleotide as described below.

Example 21

Using CE/LIF in competitive binding studies between TMR-BPDE-16-mer and unlabeled BPDE-90-mer: To observe two types of secondary complexes, we further devised a binding system using unlabeled BPDE-90-mer to compete with the labeled TMR-BPDE-16-mer for a limiting amount of the antibody. In the absence of the 90-mer, the antibody forms two complexes with the 16mer*; Ab(16mer*) and Ab(16mer*)$_2$. In the presence of BPDE-90-mer, the BPDE-90-mer competes with the 16mer* for the antibody binding sites. Several complexes containing the 90-mer may be formed, including Ab(90mer), Ab(90mer)$_2$, and Ab(16mer*)(90mer). Among these complexes, only Ab(16mer*)(90mer) is fluorescent and can be detected. The observation of Ab(16mer*)(90mer) and the accompanying decrease of the Ab(16mer*)$_2$ in the presence of the 90-mer clearly demonstrate the redistribution of the two ligands and the binding stoichiometry. The redistribution of ligands between two binding sites of the antibody cannot be observed in traditional binding assays that are based on measurement of total bound ligands.

In this study, we demonstrated that the DNA adduct and the antibody formed two complexes with the 1:1 and 2:1 stoichiometry. Binding of the antibody with a mixture of the TMR-labeled and unlabeled BPDE-16-mer showed a typical competitive binding behavior when a high concentration of the unlabeled BPDE-16-mer was used. With a lower concentration of the unlabeled BPDE-16-mer, the TMR labeled BPDE-16-mer was partially distributed into the secondary complex. The results suggest that the two binding sites of the mouse monoclonal antibody are dependent upon each other, and that the primary binding has a higher affinity than the secondary binding.

Scatchard plot is commonly used to characterize molecular binding events (Scatchard, 1949). For polyclonal antibody, Scatchard plot is curved because of the heterogeneous population of the antibody molecules. For monoclonal antibody, Scatchard plot is considered linear because monoclonal antibody is homogeneous with the same affinity and has two identical antigen-binding sites. However, this does not take into account the differences between the secondary and the primary binding. When the secondary binding is affected by primary binding, the Scatchard plot could deviate from linearity. In fact several authors have observed non-linear Scatchard plots for monoclonal antibody although reasons for the non-linearity was not discussed. It is possible that secondary binding and the redistribution may contribute to the non-linear nature of calibration curves for traditional competitive assays where the primary and secondary complexes are not separated. In traditional competitive immunoassay, the dose-response curve usually is sigmoid in shape with two asymptotes and one point of inflection (Nix, et al., 2000).

I claim:

1. A method for determining the binding affinity and/or stoichiometry of a binding complex having a binding factor and a probe, comprising:
   (a) contacting a sample comprising a binding factor selected from the group consisting of vancomycin antibody, trp operator-repressor, and staphylococcal enterotoxin A antibody with a probe comprising a fluorophore bound to one of vancomycin, staphylococcal enterotoxin A, or trp operator, wherein the probe binds to the binding factor forming a binding complex; and
   (b) separating the binding complex and unbound probe into different fractions by electrokinetic chromatography and simultaneously measuring the laser-induced fluorescence polarization of the complex wherein the fluorescence polarization measurement is conducted under conditions allowing detection of the binding complex relative to the unbound probe.

2. The method of claim 1 wherein the electrokinetic chromatography is capillary electrophoresis.

3. The method of claim 1 wherein the fluorophore is fluorescein.

4. The method of claim 1 wherein the probe has a molecular weight of less than about 20,000 daltons.

5. The method of claim 4 wherein the probe has a molecular weight of less than about 5,000 daltons.

* * * * *